United States Patent
Park et al.

(10) Patent No.: US 8,975,215 B2
(45) Date of Patent: Mar. 10, 2015

(54) METHODS FOR PRODUCING SURFACE BOUND OLIGONUCLEOTIDE ON SOLID SUBSTRATE AND USES THEREOF

(75) Inventors: Joon Won Park, Pohang (KR); Bong Jin Hong, Evanston, IL (US); Duk Hoe Kim, Pohang (KR)

(73) Assignees: Postech Foundation, Pohang (KR); Posco, Pohang-shi (KR)

( * ) Notice: Subject to any disclaimer, the term of this patent is extended or adjusted under 35 U.S.C. 154(b) by 648 days.

(21) Appl. No.: 12/619,233

(22) Filed: Nov. 16, 2009

(65) Prior Publication Data

US 2010/0210024 A1 Aug. 19, 2010

Related U.S. Application Data

(63) Continuation-in-part of application No. 12/599,719, filed as application No. PCT/IB2008/003808 on Sep. 17, 2008, now abandoned.

(60) Provisional application No. 60/973,079, filed on Sep. 17, 2007.

(51) Int. Cl.
| | |
|---|---|
| *C40B 50/14* | (2006.01) |
| *B82Y 15/00* | (2011.01) |
| *B82Y 35/00* | (2011.01) |
| *C12Q 1/68* | (2006.01) |
| *G01Q 60/42* | (2010.01) |

(52) U.S. Cl.
CPC ............ *B82Y 15/00* (2013.01); *B82Y 35/00* (2013.01); *C12Q 1/6834* (2013.01); *G01Q 60/42* (2013.01)
USPC .......................................... 506/30

(58) Field of Classification Search
None
See application file for complete search history.

(56) References Cited

U.S. PATENT DOCUMENTS

| 5,759,773 A * | 6/1998 | Tyagi et al. ............... 435/6.12 |
| 6,787,312 B2 * | 9/2004 | Bao et al. ..................... 506/39 |
| 2003/0207295 A1 * | 11/2003 | Gunderson et al. ........... 435/6 |
| 2007/0031942 A1 * | 2/2007 | Gao et al. .................. 435/91.2 |
| 2007/0128623 A1 * | 6/2007 | Park et al. ..................... 435/6 |

OTHER PUBLICATIONS

Berg et al., Biochemistry, 2002, 5th. Edition, Figure 27.28, p. 1.*

* cited by examiner

*Primary Examiner* — Karlheinz R Skowronek
*Assistant Examiner* — Lianko Garyu
(74) *Attorney, Agent, or Firm* — Don D. Cha; Hamilton DeSanctis & Cha

(57) ABSTRACT

The present invention relates to methods for producing an oligonucleotide on a solid substrate surface and methods for using the same. Some aspects of the invention provide methods for selecting a single DNA molecule reproducibily with an atomic force microscope (AFM).

13 Claims, 16 Drawing Sheets

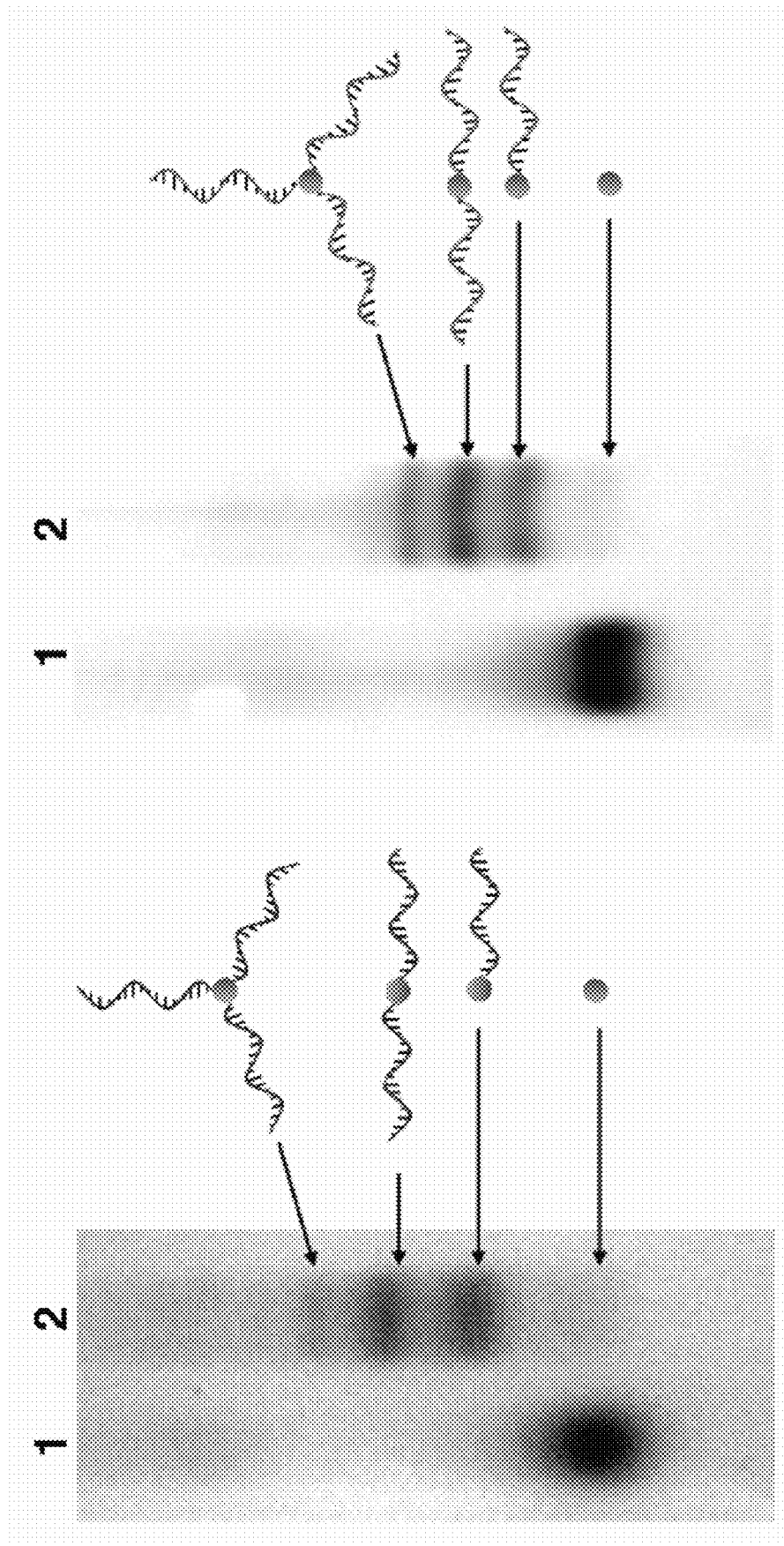

METHODS FOR PRODUCING SURFACE BOUND OLIGONUCLEOTIDE ON SOLID SUBSTRATE AND USES THEREOF

CROSS-REFERENCE TO RELATED APPLICATIONS

This application is a Continuation-In-Part Application of U.S. patent application Ser. No. 12/599,719, filed Nov. 11, 2009, which is a national phase application of PCT Patent Application No. PCT/IB08/03808, filed Sep. 17, 2008, which claims the priority benefit of U.S. Provisional Application No. 60/973,079, filed Sep. 17, 2007, all of which are incorporated herein by reference in their entirety.

FIELD OF THE INVENTION

The present invention relates to methods for producing an oligonucleotide on a solid substrate surface and methods for using the same.

BACKGROUND OF THE INVENTION

Many conventional biological assay methods use a probe that is attached to a solid substrate surface. Typically, these methods utilize a solid substrate in which a tailor-made probe is attached. In general, such methods require each solid substrate be fabricated with the desired probe. While such methods are suitable for instances where the probes are different, there are instances where different probes share a common feature. Conventional methods require that even in these instances, where many probes share a common feature, each probe must be independently fabricated and attached to a solid substrate. Such methods are analogous to a stepwise synthesis in organic chemistry, in which each piece of the molecule is made in a stepwise manner.

It is well known in organic chemistry that a convergent synthesis method typically yields a higher efficiency compared to a stepwise synthesis method. Furthermore, unlike a stepwise synthesis method, a convergent synthesis method allows an efficient synthesis of a wide variety of structurally related products from a common intermediate. Unfortunately, conventional methods for attaching a probe to a solid substrate surface often mimic a stepwise synthesis method in organic chemistry.

Therefore, there is a need for a method for attaching a probe to a solid substrate surface that is analogous to a convergent synthesis method in organic chemistry.

SUMMARY OF THE INVENTION

Some aspects of the invention provide methods for producing a surface bound oligonucleotide on a solid substrate in a manner analogous to a convergent synthesis method in organic chemistry. Typically, such methods of the invention attach separate portions of the oligonucleotide to the solid substrate using a template oligonucleotide and covalently link the unlinked oligonucleotides to produce a one-piece oligonucleotide probe. Often such methods comprise:

contacting a target oligonucleotide with a first oligonucleotide bound to a surface of a first solid substrate under conditions sufficient to produce a partially hybridized oligonucleotide complex, wherein the target oligonucleotide comprises an oligonucleotide sequence that is complementary to the first oligonucleotide sequence;

contacting a second oligonucleotide with the partially hybridized oligonucleotide complex under conditions sufficient to produce a segmented hybridized oligonucleotide complex, wherein the second oligonucleotide comprises an oligonucleotide sequence that is complementary to an unhybridized portion of the target oligonucleotide of the partially hybridized oligonucleotide complex; and contacting the segmented hybridized oligonucleotide complex with a ligase under conditions sufficient to covalently link the first oligonucleotide and the second oligonucleotide to produce a surface bound oligonucleotide complex comprising a surface bound oligonucleotide which comprises a nucleotide sequence that is complementary to the nucleotide sequence of the target oligonucleotide.

In some embodiments, the step of contacting the target oligonucleotide with the first substrate surface comprises contacting the first oligonucleotide with the target oligonucleotide that is bound to a surface of a second solid substrate under conditions sufficient to hybridize the first oligonucleotide to a portion of the target oligonucleotide.

Yet in other embodiments, the second oligonucleotide further comprises an additional oligonucleotide such that the segmented hybridized oligonucleotide complex comprises at least a portion of the second oligonucleotide that is not hybridized to the target oligonucleotide. Within these embodiments, in some instances methods of the invention further comprise the step of ligating at least a portion of the second oligonucleotide that is not hybridized to the target oligonucleotide prior to said step of forming a covalent link between the first oligonucleotide and the second oligonucleotide.

Still in other embodiments, the first or the second oligonucleotide can also comprise a label. In this manner, the resulting surface bound oligonucleotide can be labeled for a particular application. Exemplary labels include, but are not limited to, fluorescent labels, radio active labels, labels that can change frequency of emission, metals such as gold, nanowires, nanotubes, nanoparticles as well as other types of labels known to one skilled in the art. Alternatively, or in addition, the first or the second oligonucleotide can comprise a ligand a receptor, or any other moiety that is useful for assaying. In this manner, the resulting oligonucleotide can include a tethered moiety that is useful in a wide variety of applications.

In other embodiments, methods can further comprise a step of subjecting the surface bound oligonucleotide complex under conditions sufficient to remove the target oligonucleotide from the surface bound oligonucleotide complex to produce the first substrate surface bound oligonucleotide that comprises a complementary nucleotide sequence of the target oligonucleotide. As discussed in detail below, the oligonucleotide complex can include other components such as a protein or other peptide, a ligand or a receptor, and other molecules that are useful in various assays or detections.

In some embodiments, the first oligonucleotide is bound to the first substrate surface by a first linker. Within these embodiments, in some instances the first linker comprises a dendron. In some cases, the dendron is of the formula:

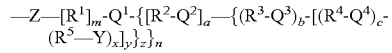

where
each of m, a, b, and c is independently 0 or 1;
x is 1 when c is 0 or when c is 1, x is an integer from 1 to the oxidation state of $Q^4$–1;
y is 1 when b is 0 or when b is 1, y is an integer from 1 to the oxidation state of $Q^3$–1;

z is 1 when a is 0 or when a is 1, z is an integer from 1 to the oxidation state of $Q^2-1$;

n is an integer from 1 to the oxidation state of $Q^1-1$;

$Q^1$ is a central atom having the oxidation state of at least 3;

each of $Q^2$, $Q^3$ and $Q^4$ is independently a branch atom having the oxidation state of at least 3;

each of $R^1$, $R^2$, $R^3$, $R^4$, and $R^5$ is independently a linker;

Z is a functional group linked to the first oligonucleotide; and each of Y is independently a functional group, wherein a plurality of Y are attached to the first solid substrate surface, provided the product of n, x, y, and z is at least 3. In some particular embodiments, Z comprises a heteroatom selected from the group consisting of N, O, S, P, and a combination thereof. It should be appreciated that typically Z does not include what one skilled in the art of organic chemistry to be an unstable functional group such as peroxides, —O—S— linkage, etc. In some instances Z comprises a functional group selected from the group consisting of —NR—C (=X)—O—, —O—C(=X)—O—, —NR—C(=X)—, —O—C(=X)—, wherein X is N, O, or S, and R is hydrogen, alkyl, cycloalkyl, aralkyl, aryl, or (cycloalkyl)alkyl.

In some embodiments, each of $R^1$, $R^2$, $R^3$, $R^4$, and $R^5$ is independently a linker comprising 4 to 20 linker chain atoms, wherein each linker chain atom is independently selected from the group consisting of C, O, N, S, and P. Typically, the linker does not include what one skilled in the art of organic chemistry to be an unstable functional group such as peroxides, —O—S— linkage, etc. In some instances, the linker comprises a carbon atom chain with a functional group that allows a linkage to respective Q moiety. For example, the linker can include a functional group similar to those described for Z. Still in other instances, the linker can include in the chain an oxygen atom (e.g., an ether linkage), a nitrogen atom (e.g., an amino linkage), a sulfur atom (e.g., a thioether linkage), etc.

Methods of the invention can be used to attach oligonucleotides to any suitable solid substrates known to one skilled in the art including, but not limited to, glass, porous solids, silicon wafers, metals, ceramics, alloys, polymers, etc. Moreover, methods of the invention are applicable to porous solids as well as non-porous solids. In some embodiments, the first solid substrate is an atomic force microscope tip. In some instances, methods of the invention are used to attach 5 or less, typically 3 or less, and often a single surface bound oligonucleotide. Methods of the invention typically produce an oligonucleotide which comprises a nucleotide sequence that is complementary to the nucleotide sequence of the target oligonucleotide.

Yet in other embodiments, the first oligonucleotide comprises at least 10, typically at least 20, often at least 30, and more often at least 50 oligonucleotide sequence. Still in other embodiments, the second oligonucleotide comprises at least 10, typically at least 20, often at least 30, and more often at least 50 oligonucleotide sequence.

Other aspects of the invention provide methods for attaching a single-stranded oligonucleotide on a first solid substrate surface. Typically, such methods comprise:

contacting a single-stranded target oligonucleotide with a first single-stranded oligonucleotide bound to a surface of a first solid substrate under conditions sufficient to produce a first hybridized partially double-stranded oligonucleotide complex, wherein the target oligonucleotide comprises a nucleotide sequence that is complementary to the nucleotide sequence of the first single stranded oligonucleotide;

contacting a second oligonucleotide with the first hybridized partially double-stranded oligonucleotide complex under conditions sufficient to produce a segmented hybridized double-stranded oligonucleotide complex, wherein the second oligonucleotide comprises a nucleotide sequence that is complementary to an unhybridized portion of the target oligonucleotide of the first hybridized partially double-stranded oligonucleotide complex;

contacting the segmented hybridized double-stranded oligonucleotide complex with a ligase under conditions sufficient to covalently link the first oligonucleotide and the second oligonucleotide to produce a first solid substrate surface bound double-stranded oligonucleotide complex comprising a nucleotide sequence that is complementary to the nucleotide sequence of the target oligonucleotide; and subjecting the first solid substrate surface bound double-stranded oligonucleotide complex to conditions sufficient to denature the first solid substrate surface bound double-stranded oligonucleotide complex to produce a first solid substrate surface bound single-stranded oligonucleotide, wherein the first solid substrate surface bound single-stranded oligonucleotide comprises nucleotide sequence that is complementary to the nucleotide sequence of the target oligonucleotide.

Still other aspects of the invention provide methods for determining the presence of a particular oligonucleotide in a sample. Such methods typically utilize a probe oligonucleotide that comprises a single-stranded oligonucleotide bound to the solid substrate surface produced by a method described herein. Typically, methods for determining the presence of a particular oligonucleotide in a sample comprise:

contacting the sample with a probe oligonucleotide bound to a solid substrate surface under conditions sufficient to produce a probe-ligand hybridized complex when the sample comprises a particular oligonucleotide having a nucleotide sequence that is complementary to the nucleotide sequence of the probe oligonucleotide, wherein the probe oligonucleotide comprises a single-stranded oligonucleotide bound to the solid substrate surface produced by a method described herein; and determining the presence of the probe-ligand hybridized complex on the solid substrate surface, wherein the presence of the probe-ligand hybridized complex on the solid substrate surface is indication that the particular oligonucleotide is present in the sample.

In some embodiments, the first solid substrate is an atomic force microscope tip. In some instances, the atomic force microscope tip comprises a single surface bound oligonucleotide probe.

BRIEF DESCRIPTION OF THE DRAWINGS

FIG. 6A is a gel image of the AuNP-DNA conjugate mixture. The phosphine-capped AuNPs were injected into column 1, and the various products were separated in column 2.

FIG. 6B is a gel image after conjugating the DNAs for the second hybridization with AuNPs. Reference materials were injected at column 1, and various isomers were separated in column 2.

DETAILED DESCRIPTION OF THE INVENTION

Figure 1A:
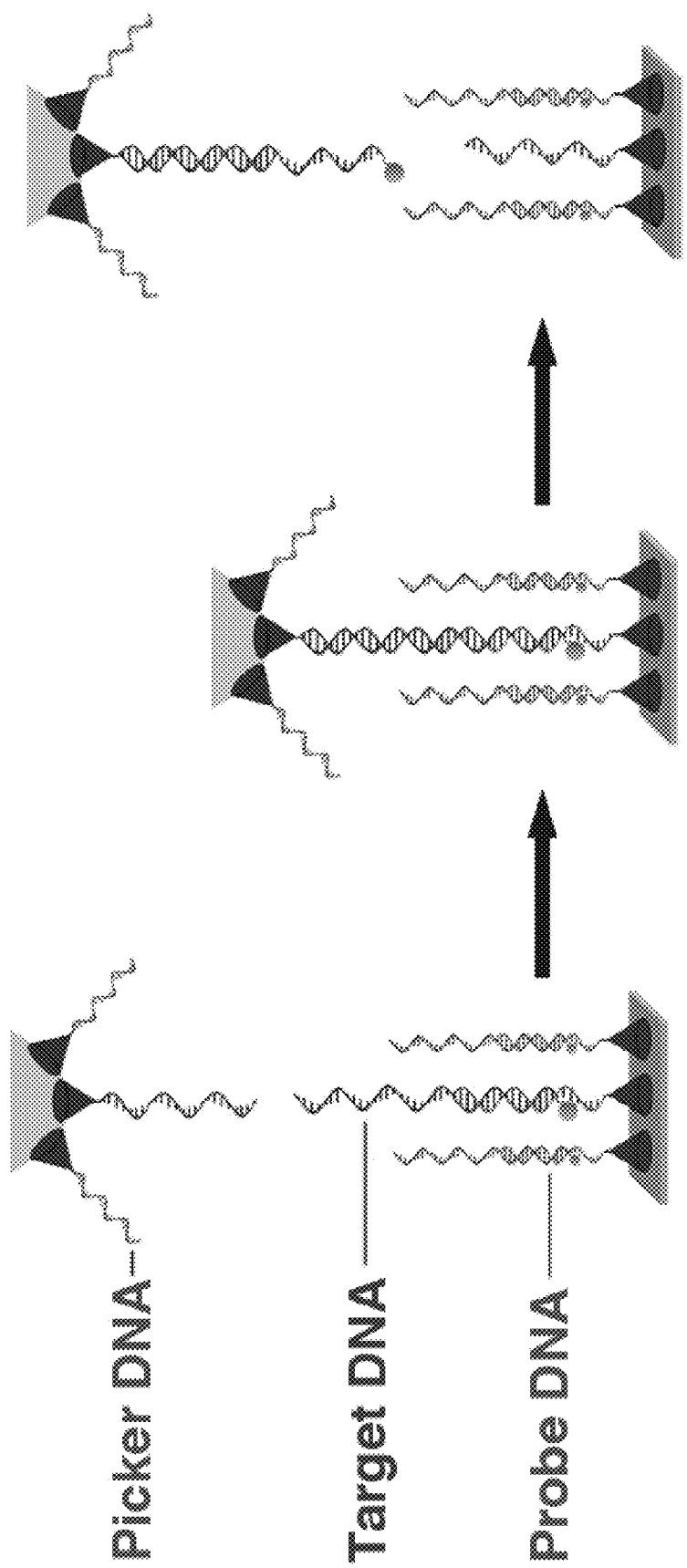
FIG. 1A is a schematic illustration of picking a single target DNA molecule with AuNP AFM. For clarity, DNA molecules at the center are enlarged.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

The term "dendrimer" refers to a repeatedly branched molecules. Typically a dendrimer is characterized by a core, at least one interior branched layer, and a surface branched layer (see, e.g., Petar et al. in *Chem. in Britain*, pp. 641-645, August 1994). A "dendron" is a species of dendrimer having branches emanating from a focal point or a central atom, which is or can be joined to a core, either directly or through a linking moiety to form a dendrimer. Dendrimer can comprise two or more dendrons joined to a common core. Dendrons include, but are not limited to, symmetrical and asymmetrical branching dendrimers, cascade molecules, arborols, and the like. Each branch arm of the dendrimer and dendron can be of equal or different in length.

As used herein, the terms "nucleotide" and "nucleic acid" are used interchangeably herein and refer to both natural and synthetic nucleotide molecules that can be used in place of naturally occurring bases in nucleic acid synthesis and processing, e.g., enzymatic as well as chemical synthesis and processing. Thus, nucleotide includes modified nucleotides capable of base pairing and optionally synthetic bases that do not comprise adenine, guanine, cytosine, thymidine, uracil or minor bases. For example, "nucleotide" includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and nonnucleotide bridges such as polyethylene glycol, aromatic polyamides and lipids. In addition, a nucleotide can be a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. A "subsequence" or "segment" refers to a sequence of nucleotides that comprise a part of a longer sequence of nucleotides.

The term "oligonucleotide" refers to a nucleic acid polymer comprising at least two, typically at least five, often at least ten, and more often at least twenty nucleotides. Typically, an oligonucleotide comprises from two to about one thousand nucleotides, often two to about five hundred nucleotides, and more often two to about three hundred nucleotides.

As used herein, the terms "solid support" and "solid substrate" are used interchangeably herein and refer to a composition comprising an immobilization matrix such as but not limited to: insolubilized substances; woven or nonwoven fibers; crystals; membranes; insoluble polymers; plastics; glass; beads; biological or biocompatible or bioerodible or biodegradable polymers or matrix; microparticles; nanoparticles; semiconductor materials; synthetic (e.g., organic) metals; synthetic semiconductors; metals; alloys; elements; compounds; minerals; synthetic, cleaved, etched, lithographed, printed, machined and microfabricated slides, devices, structures and surfaces; silicon; silicates; ceramics; wood; paper; cardboard; cotton; wool; cloth; woven and nonwoven materials and fabrics; resins; chromatography supports; mica; microspheres; and nanospheres. Microstructures and nanostructures can include, without limitation, microminiaturized, nanometer-scale and supramolecular probes, tips, bars, pegs, plugs, rods, sleeves, wires, filaments, and tubes.

Unless the context requires otherwise, the term "ligand" refers to any substance that is capable of binding selectively with a probe. A ligand can be an antigen, an antibody, an oligonucleotide, an oligopeptide (including proteins, hormone, etc.), an enzyme, a substrate, a drug, a drug-receptor, cell surface, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, structural molecules, effector molecules, selectable molecules, biotin, digoxigenin, crossreactants, analogs, competitors or derivatives of these molecules as well as library-selected nonoligonucleotide molecules capable of specifically binding to selected targets and conjugates formed by attaching any of these molecules to a second molecule, and any other molecule that binds selectively with a corresponding probe.

It should be appreciated that the terms "ligand" and "receptor" do not refer to any particular substance or size relationship. These terms are only operational terms that indicate selective binding between the ligand and the corresponding probe where the moiety that is bound to a substrate surface is referred to as a probe and any substance that selectively binds to the probe is referred to as a ligand. Thus, if an antibody is attached to the substrate surface then the antibody is a probe and the corresponding antigen is a ligand. However, if an antigen is attached to the substrate surface then the antigen is a probe and the corresponding antibody is a ligand.

The term "complementary" means that one nucleic acid is identical to, or hybridizes selectively to another nucleic acid molecule. Selectivity of hybridization exists when hybridization occurs that is more selective than total lack of specificity. Typically, selective hybridization will occur when there is at least about 55% identity over a stretch of at least 14-25 nucleotides, typically at least 65%, often at least 75%, and more often at least 90%.

The terms "identical" or percent "identity," in the context of two or more nucleic acids, refer to two or more sequences or subsequences that are the same or have a specified percentage of nucleotides that are the same, when compared and aligned for maximum correspondence, as measured using a sequence comparison algorithm such as those described below for example, or by visual inspection.

The phrase "substantially identical," in the context of two nucleic acids, refers to two or more sequences or subsequences that have at least 75%, typically at least 80% or 85%, often at least 90%, 95% or higher nucleotide identity, when compared and aligned for maximum correspondence, as measured using a sequence comparison algorithm such as those described below for example, or by visual inspection. Generally, the substantial identity exists over a region of the sequences that is at least about 40-60 nucleotides in length, in other instances over a region at least 60-80 nucleotides in length, in still other instances at least 90-100 nucleotides in length, and in yet other instances the sequences are substantially identical over the full length of the sequences being compared, such as the coding region of a nucleotide for example.

Atomic Force Microscope

The present invention will be described with regard to immobilizing an oligonucleotide on an Atomic Force Microscope (AFM) tip. However, it should be appreciated that methods of the invention described herein are not limited to attaching oligonucleotide to an AFM tip but rather is generally applicable to attaching a wide number of oligonucleotides to any solid substrate surface.

Initially, Atomic Force Microscope (AFM) was developed for the observation of solid surface topography. Currently, AFM is used in a wide range of applications including, but not limited to, measuring interactions between biomolecules such as in drug screening. Ability to measure the interaction between biomolecules is a powerful analytical tool that allows identification of various association and dissociation phenomena between biomolecules. For example, AFM is sometimes used to find the position and distribution of a specific ligand on the cell surface. While fluorescence microscope and radioisotope have been used to identify the distribution of ligands on the cell surface, these methods can only show distribution of tens to hundreds of conglomerated ligands in the micron-sized scale. In contrast, measurement of interacting forces between biomolecules with AFM provides more accurate and detailed analysis allowing a possibility of tracking individual position of the nano-sized ligands and observation of individual life phenomena.

Unfortunately, conventional methods of immobilizing biomolecules onto the AFM tip typically result in having biomolecules being attached not only on or near the apex of the tip but on various AFM tip locations, thus leading to a relatively low resolution of AFM. To overcome such a limitation, some have used high dilution methods or mixed monolayer methods when introducing the biomolecules onto the AFM tip. Although these methods reduce the relative population density of biomolecules immobilized on the AFM tip, they have not been successful in effectively immobilizing the biomolecules specifically on the apex of the AFM tip and in many instances the biomolecules could not be immobilized on the apex of the AFM tip.

Besides aforementioned studies on the measurement of interaction between biomolecules by means of AFM, other applications of the AFM have recently been attempted. For example, currently some have attempted to introduce compounds like carbon nanotubes or nanoparticles onto the apex of the AFM tip. But currently available methods are not adapted for selectively modifying the apex of the AFM tip.

Methods of the invention allow attaching a wide number of oligonucleotides to any solid substrate surface including, but not limited to, on or near the apex of the AFM tip. When applied to attaching oligonucleotides to an AFM tip, methods of the invention can be used to attach five or less, typically three or less, and often a single oligonucleotide molecule on the AFM tip. Moreover, methods of the invention can be used to attach an oligonucleotide near, often at, the apex of AFM tip.

Single-molecule force spectroscopy has revealed valuable information about the physicochemical properties of individual molecules. In particular, AFM is an important tool because it can sense pN-scale forces, and generate high resolution images of solid surfaces and biological samples, including cells. Additionally, the instrument can be used as a nanomachine to pick up and transport a single molecule to a specific position. For example, using single-molecule fluorescence microscopy, some have shown that AFM could pick a single DNA strand from a depot area and deposit it onto a target area. While the tool has been employed widely, one common challenge is realizing the single molecular interaction while avoiding multimolecular interactions. In the above mentioned DNA transport, it is believed that the AFM tip recognized the single DNA-DNA interaction with about 35% success rate, and the tip was treated at the "trash can" area when multiple DNAs were captured. While carbon nanotube tips have found numerous applications, especially in topographical imaging, double interactions have been observed in some cases. Therefore, the tethering of a single molecule to the apex of an AFM tip is expected to eliminate the common difficulties and to extend the application of this nano-tool.

Figure 1B:
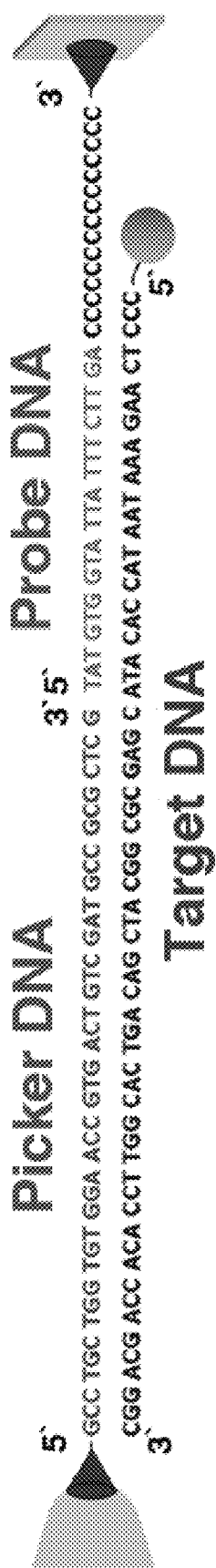
FIG. 1B provides an illustrative picker DNA (SEQ ID NO:1), probe DNA (SEQ ID NO:2) and target DNA (SEQ ID NO:3) that are used for picking a single DNA molecule as illustrated in FIG. 1A.
Figure 1C:
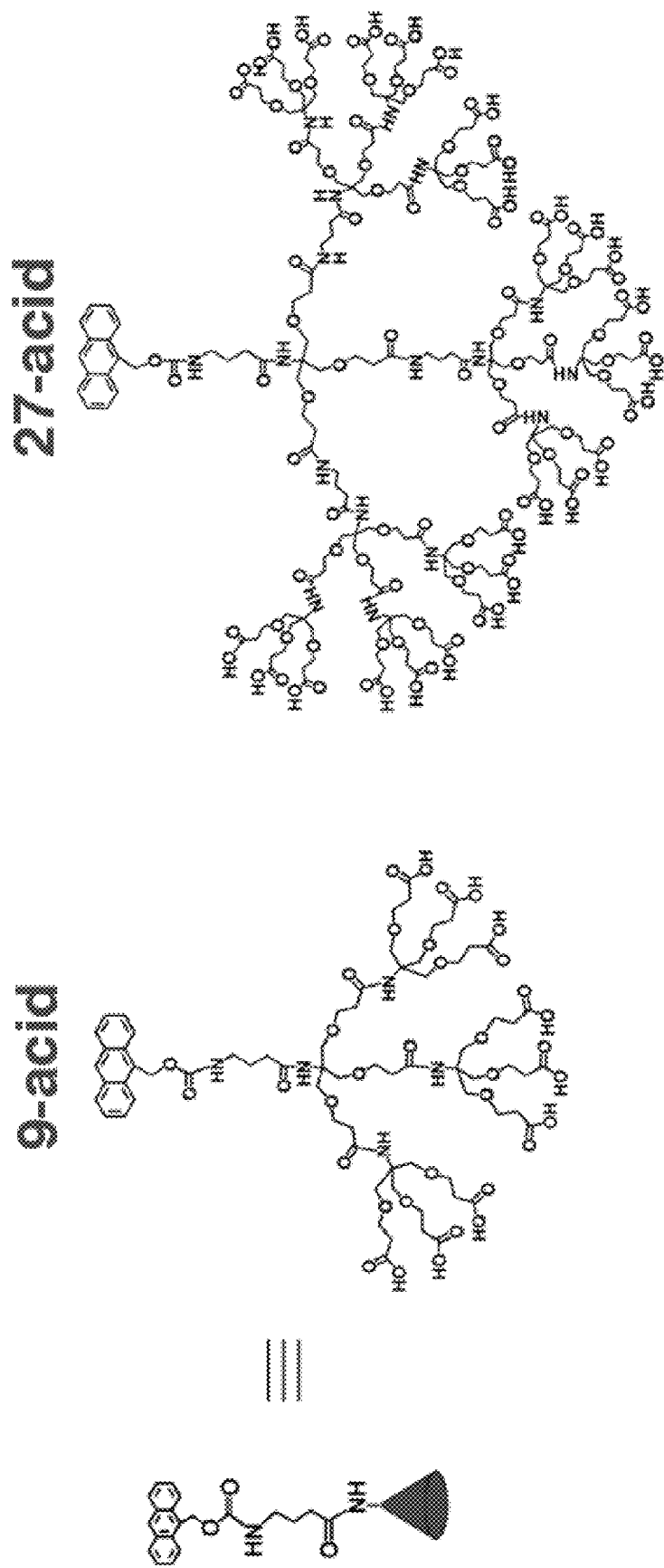
FIG. 1C shows structures of the 9-acid and 27-acid.

The present inventors have previously discovered that the dendron-modified AFM tip enabled reproducible observation of the binding phenomenon and single peaks in the force-distance curve. This modified AFM tip was used to selectively hybridize a single DNA molecule, and obtained transmission electron microscopy (TEM) images for visualization. As schematically illustrated in FIG. 1, a picker DNA (40-mer) was immobilized on the dendron-modified AFM tip. A probe DNA (35-mer) immobilized on the dendron-modified substrate was hybridized with a target DNA (63-mer) that had a gold nanoparticle at its 5'-end. A cycle comprising of the approach and the subsequent retraction was expected to transfer the target DNA from the substrate to the tip due to a larger (i.e., stronger) interaction force between the picker DNA and the target DNA.

Figure 5A:
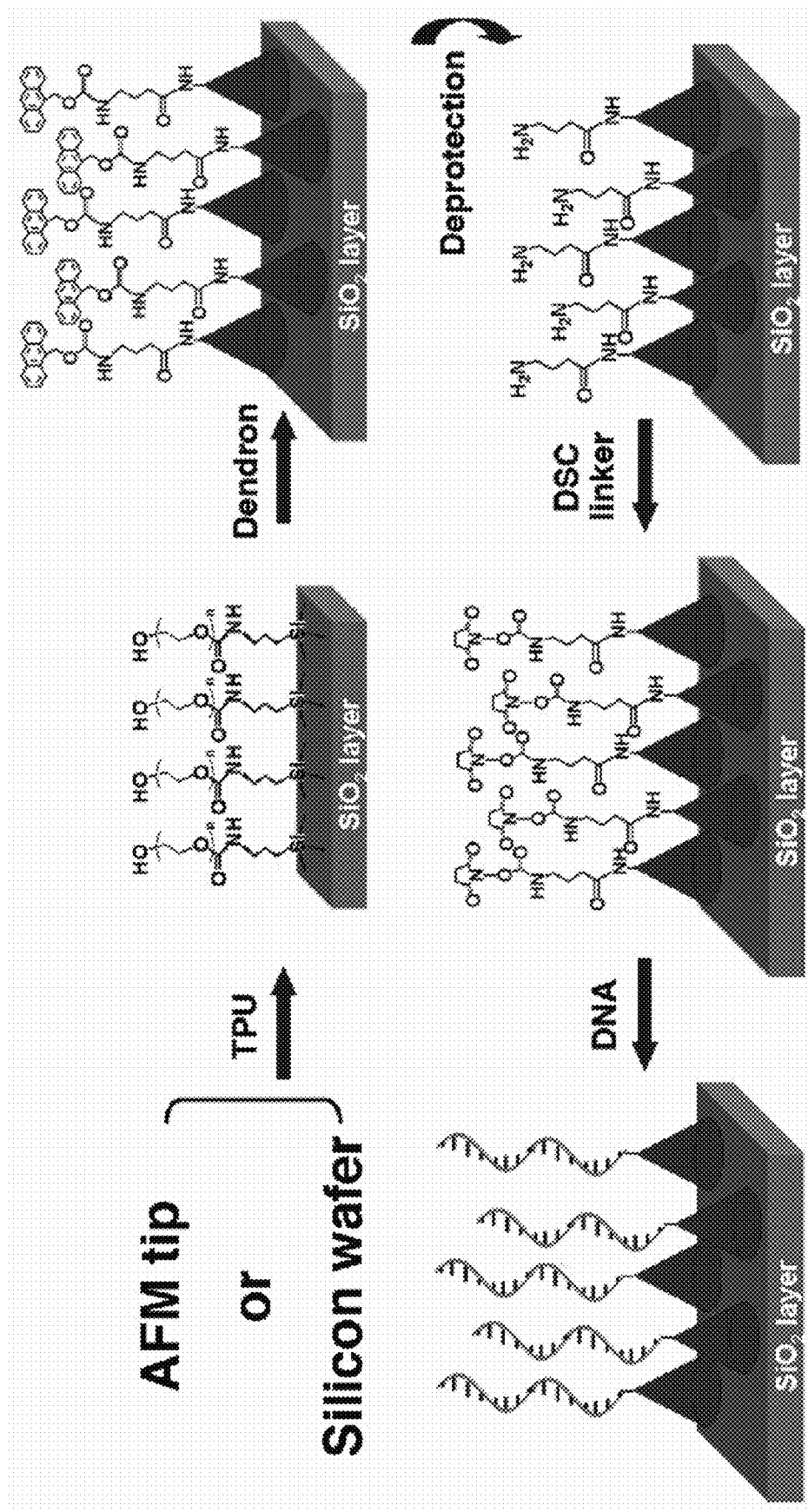
FIG. 5A (S1A) is a schematic diagram illustrating how to generate the dendron-modified substrate and AFM tip, and how to conjugate a DNA probe molecule to the dendron apex.
Figure 5B:
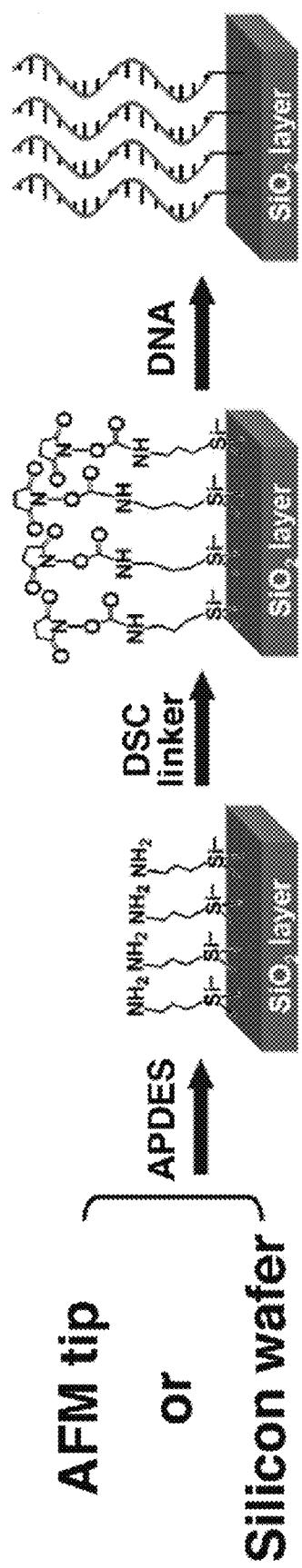
FIG. 5B is a schematic diagram showing treatment with APDES and the subsequent steps for the control experiments.

Each substrate and AFM tip was treated with N-(3-(triethoxysilyl)propyl)-O-polyethyleneoxide urethane as the first step of the modification. Then, a dendron was introduced on the silylated surface by self-assembly (see FIGS. 5A and 5B). After introduction of the dendron layer, the DNAs were covalently attached to the dendron apex. The upper 20-bp of the probe DNA were designed to capture the target DNA, and 15-bp of cytosine were added to provide more flexibility and extra space for the gold nanoparticle tethered to the target DNA (FIG. 1B). Part of the 63-bp target DNA was designed to hybridize with the probe DNA; the other longer part was complementary to the 40-bp picker DNA on the AFM tip. The present inventors have discovered that use of a 9-carboxylic acid terminated dendron is useful for studying DNA-DNA interactions. The present inventors have also discovered that a 27-carboxylic acid terminated dendron is useful for mapping purposes. As discussed in the Example section, AFM tips coated with either 9- or 27-acid were used to investigate the effect of the lateral spacing on the picking. The target DNA was conjugated with a commercially available 5 nm gold nanoparticle (AuNP). To avoid possible complications, particles with one target DNA molecule were isolated through 3% agarose gel electrophoresis (see FIGS. 6A-C).

Transmission electron microscopy (TEM) images of 9-acid modified AFM tips and substrates were taken after picking. Two out of the eleven tips had an AuNP at the top when a single cycle of approach and retraction was performed, while one tip had two AuNPs. Five cycles were allowed to increase the success yield, and resulted in three tips with a single AuNP and one tip with two AuNPs out of 9 cases. When five cycles were performed at five different spots (for a total of 25 cycles), further increases in the yield (seven tips with a single AuNP out of 16 cases) were realized, and three tips with two AuNPs and one tip with four AuNPs were observed.

Figure 2:
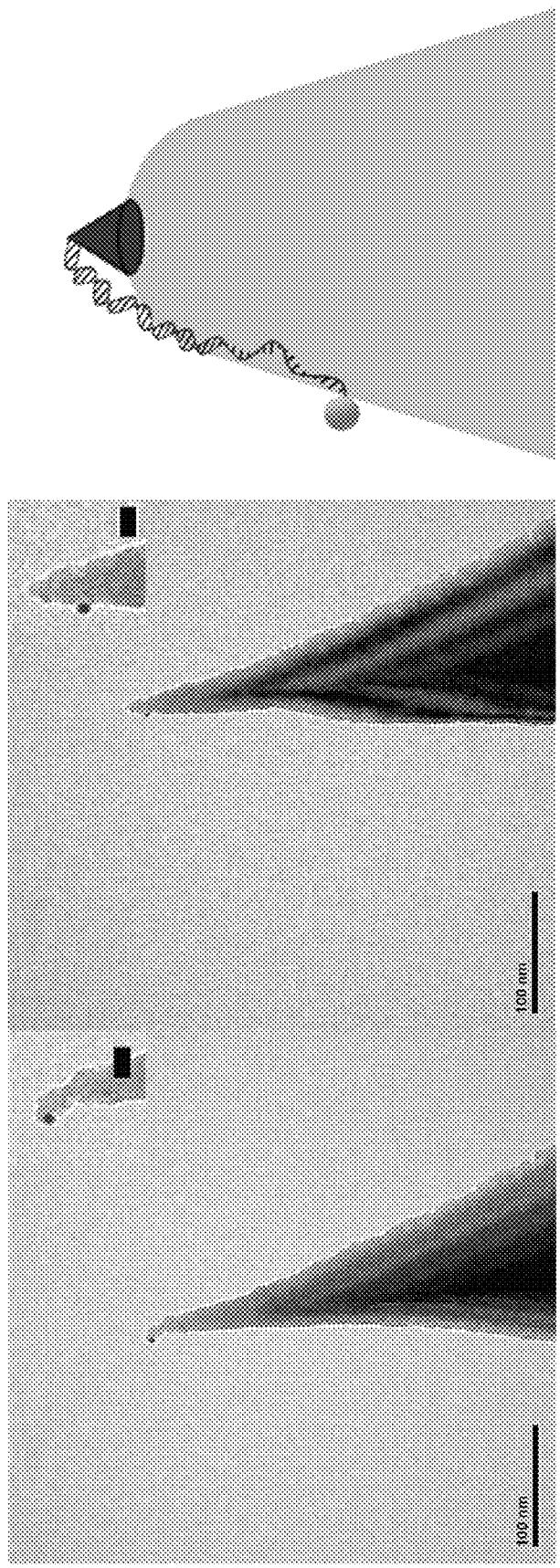
FIG. 2 shows transmission electron microscopy (TEM) images of the AFM tips after picking. Images taken after picking a DNA-AuNP conjugate from the substrate (inset scale bars, 10 nm). In some cases, the AuNP was very close to the top of the tip (left image), but more frequently the AuNP was away from the top (right image). The right schematic diagram illustrates the position of the AuNP.
Figure 7:
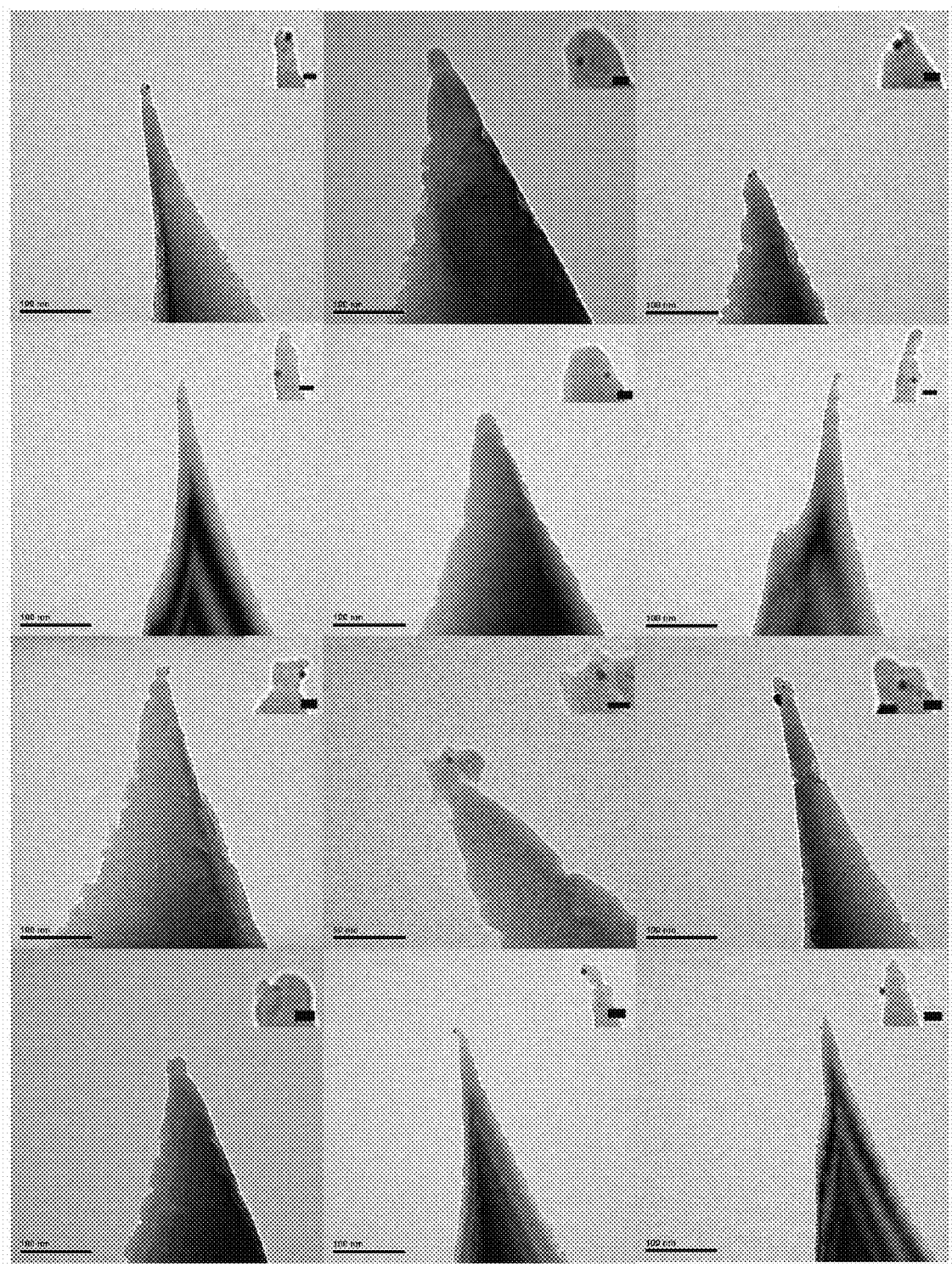
FIG. 7 is TEM images of additional AFM tips capturing a single target DNA molecule (inset scale bars, 10 nm). Picking was performed with five cycles at five different spots.
Figure 8:
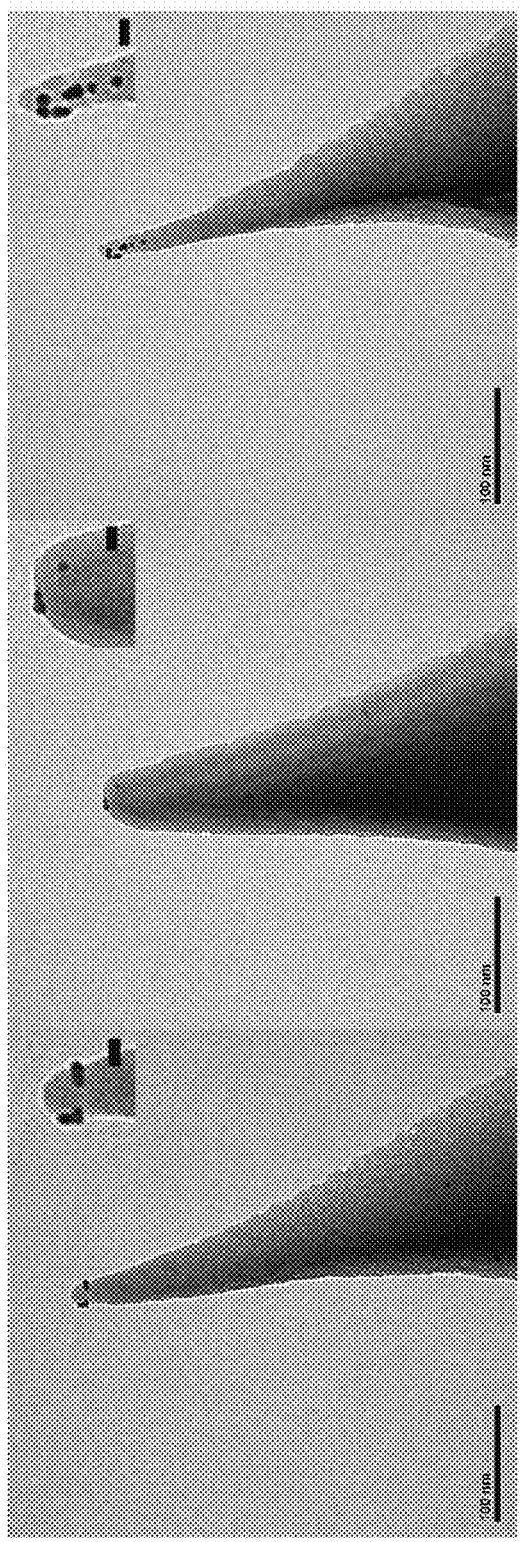
FIG. 8 is TEM images of AFM tips from the control experiments (inset scale bars, 10 nm).
Figure 9:
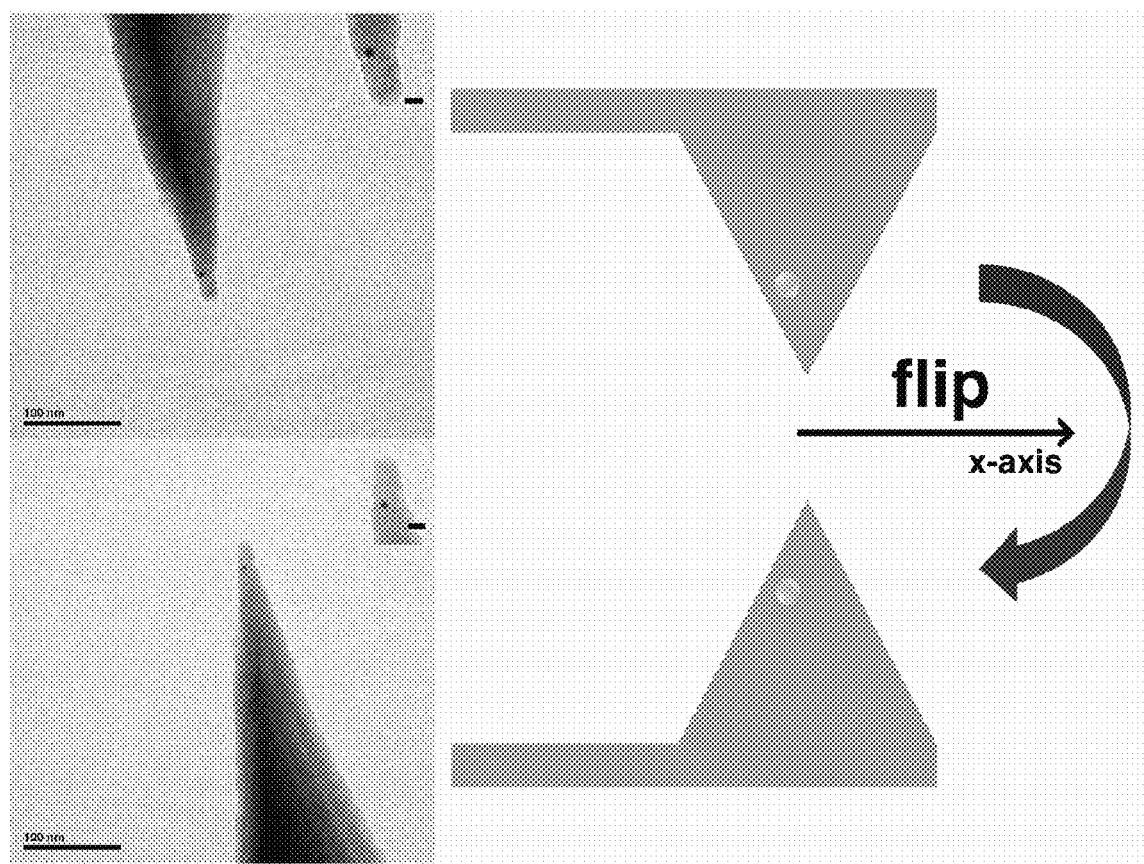
FIG. 9 is TEM images of an AFM tip before and after flipping around the x-axis (inset scale bars, 10 nm). After getting a TEM image of a tip, the tip was rotated 180° around the x-axis. A single AuNP was observed in both cases, and the position of the AuNP after flipping matched expectations.

To identify a condition eliminating or reducing the probability of picking multiple AuNPs, tips and substrates coated with a larger dendron, i.e., 27-carboxylic acid terminated dendon, were employed. Various picking cycles were examined, and tips with multiple AuNPs were not observed. With five cycles at a spot, five out of the 10 tips showed a single AuNP. This yield was increased to 75% (12 out of 16) when the picking was performed with the five cycles at five different spots (see FIG. 7). Picking at ten different spots (a total of 50 cycles) also showed a yield of 75% (9/12). While the yield was similar to the former cases (4/9 and 10/16), it was surprising and unexpected that picking multiple DNAs was avoidable with the use of the larger dendron. The observed distance between the AuNP and the top of the tip was about 34 nm or less. Because the DNA could acquire arbitrary conformations in the drying and evacuation steps, and since the maximal distance should be within the combined length of the stretched DNA and the linkers, the observed variation seems reasonable (FIG. 2). As control experiments, pickings were performed with aminosilylated tips and substrates; the TEM showed that more than 3 AuNPs were picked at the above optimized condition (see FIG. 8).

Figure 10:
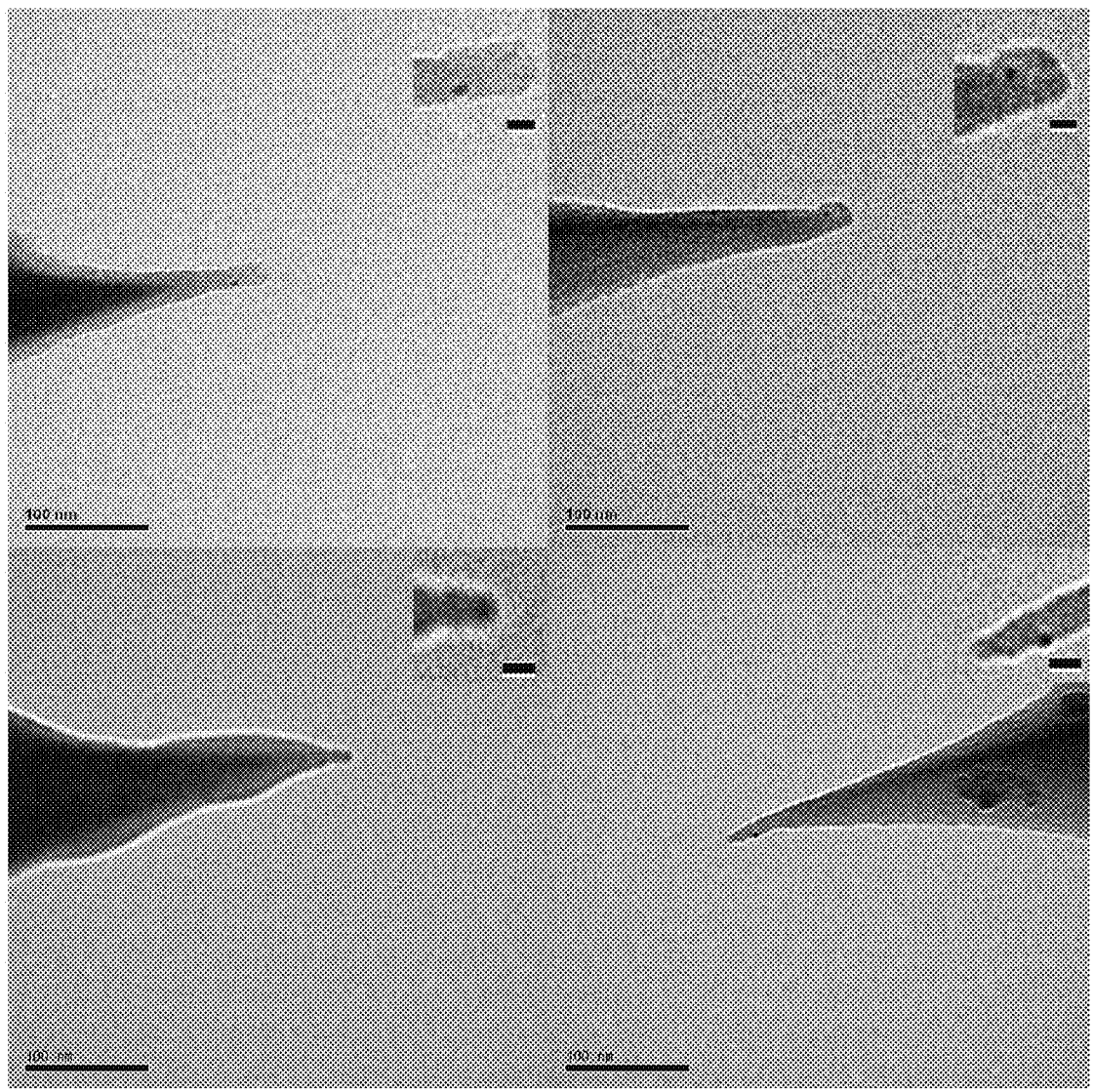
FIG. 10 is TEM images of an AFM tip in an experiment to determine influence of a relatively fast tip velocity on capturing a single target DNA molecule. The tip velocity was fixed at 10 μm/s, and the z-range was set to 5 μm. Five cycles were allowed at five different spots (a total of 25 cycles), and out of nine cases four tips had a single AuNP (inset scale bars, 10 nm).
Figure 11:
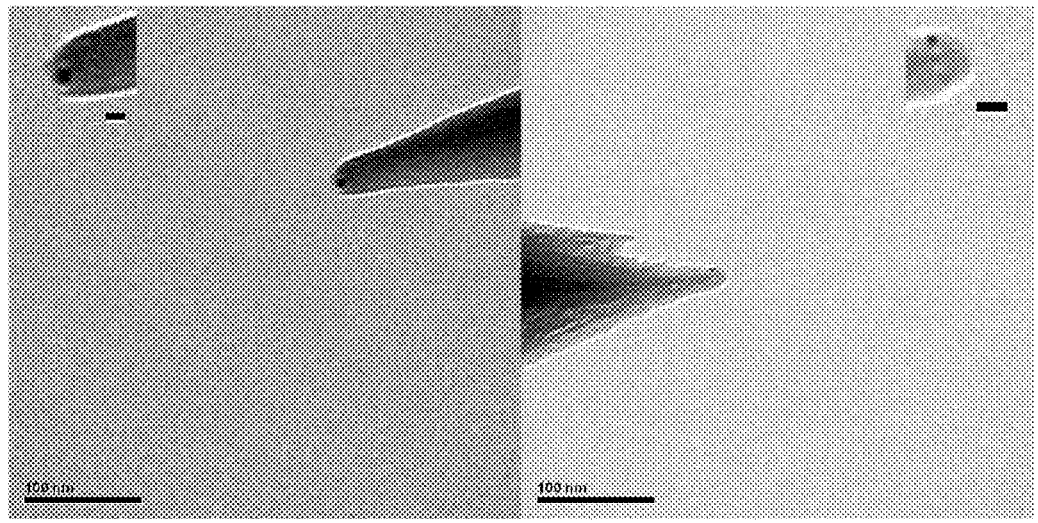
FIG. 11 is TEM images of an AFM tip in an experiment to determine influence of a relatively slow tip velocity on capturing a single target DNA molecule. The tip velocity was fixed at 0.01 μm/s, and the z-range was set to 100 nm. Five cycles were allowed at five different spots (a total of 25 cycles), and out of nine cases two tips had a single AuNP (inset scale bars, 10 nm).
Figure 12:
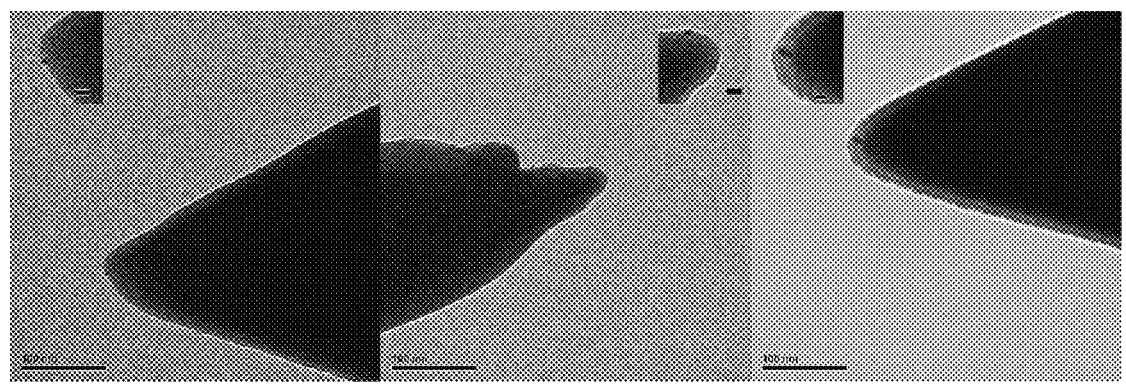
FIG. 12 is TEM images of an AFM tip in an experiment to determine the influence of a larger tip radius on capturing a single target DNA molecule. The tip velocity was fixed at 0.2 μm/s, and the z-range was set to 500 nm. Five cycles were allowed at five different spots (a total of 25 cycles). While the yield was comparable, the tip picked either a single DNA (as in the left two images) or two DNAs (as in the right side image) (inset scale bars, 10 nm).

Influence of the tip velocity as well as the tip radius to the picking efficiency was also examined. It was observed that a fast (e.g., 10 μm/s) and a slow tip velocity (e.g., 0.01 μm/s) reduced the picking yield to 44% and 22%, respectively (see FIGS. 10 and 11). Without being bound by any theory, it is believed that the shortened contact time and the reduced force value difference may be responsible for these observations. TEM images showed that in instances where AFM tips were broad (or dull), picking that produced attachment had either a single AuNP or two AuNPs (see FIG. 12). The examination showed that the approach enabled typical AFM tips to pick a single DNA, while there is a chance to pick more than single DNA when the tip radius was unusually large.

Figure 3:
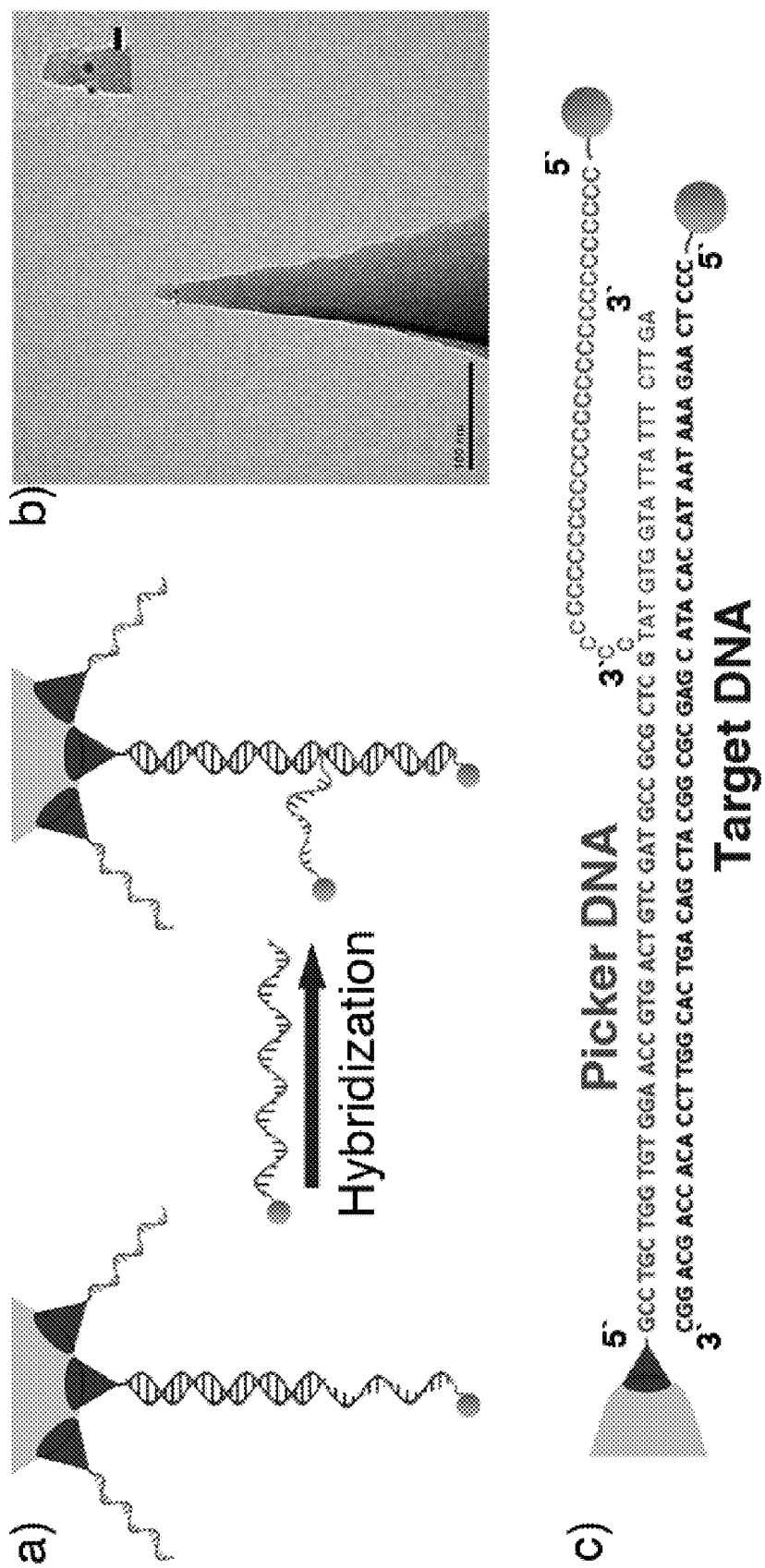
FIG. 3A shows a schematic diagram showing hybridization with the picked single DNA. For visualization, a DNA-AuNP conjugate was also employed.
FIG. 3B shows a TEM image of the resulting AFM tip of FIG. 3A (inset scale bar, 10 nm).
FIG. 3C provides an illustrative picker DNA (SEQ ID NO:4), probe DNA (SEQ ID NO:5) and target DNA (SEQ ID NO:6) that are used for post-modification of AFM tip of FIG. 3A.

The single strand part of the picked target DNA was utilized for the subsequent chemical conversion (FIG. 3). In order to demonstrate a single molecule chemistry with the single DNA picked by AFM, a 50-bp DNA that had a tethered AuNP at its 5'-end and complementary to 20-bp of the target DNA was allowed to hybridize. TEM showed that the AFM tip had two AuNPs near the top, and the distance between them (ca. 10 nm) was within the expected range. The image confirmed the identity of the target DNA picked by the above manipulation and the binding mode between the picker and target DNAs.

Figure 4:
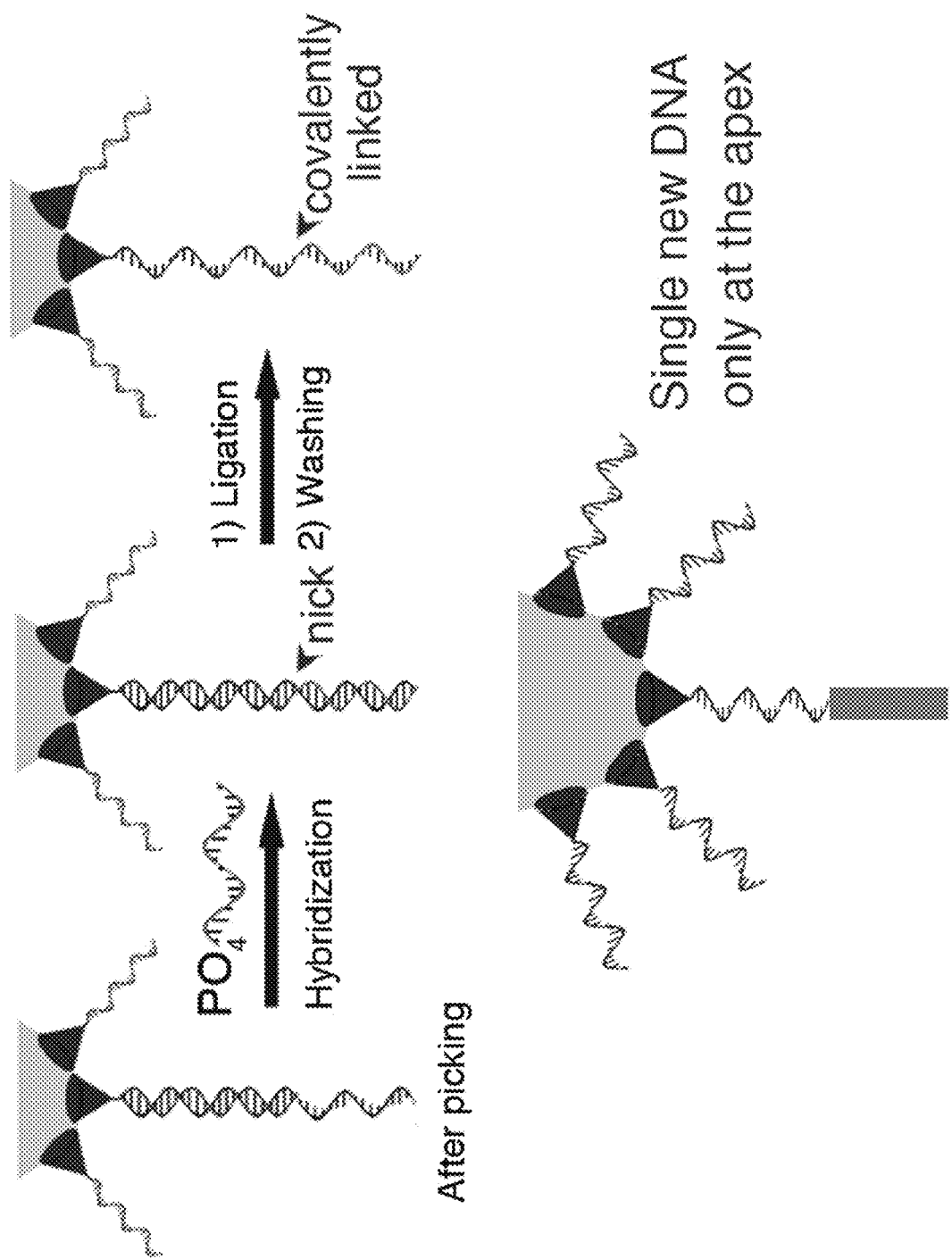
FIG. 4 is a schematic illustration of processes for preparing an AFM tip having a single DNA conjugated with the DNA at the apex. After picking the target DNA, hybridization with a new DNA, ligation, and washing were followed. A single copy of new DNA was introduced only at the apex of the AFM tip.
Figure 13:
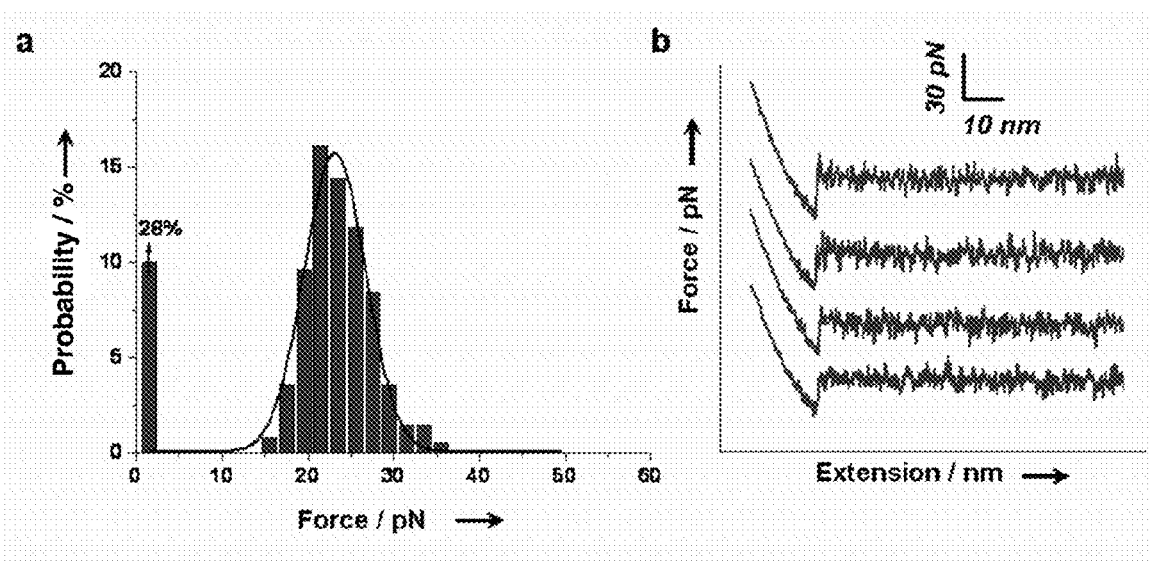
FIG. 13A is a histogram of unbinding force values recorded at a loading rate of 0.54 μm sec-1 for interactions between the 20-mer DNA on the AFM tip and the complementary DNA immobilized on the commercially available aldehyde-terminated slide.
FIG. 13B shows representative force-extension curves for interactions between the 20-mer DNA on the AFM tip and the complementary DNA immobilized on the commercially available aldehyde-terminated slide.

In some embodiments, a second hybridization is applied to covalently conjugate a new single molecule at the apex (see FIG. 4). After picking the target DNA, a 20-mer DNA of which sequence is complementary to the single strand part of the target DNA was allowed to hybridize. Through the ligation process, 5'-end of the 20-mer and 3'-end of the picker DNA were covalently linked. Stringent washing removed the target DNA from the tip. To confirm the single presence of the 20-mer DNA at the apex, the force between the tip and a substrate immobilizing the complementary DNA was measured. For this end, commercially available generic aldehyde slides were employed for the substrates, and only single rupture events were expected even with the less controlled substrates. The force-extension curves with a single peak were obtained (see FIG. 13). Gaussian fitting gave the probable rupture force of 23±1 pN. Such a process can be used to link a single copy of various molecules at the apex of AFM tips as long as the molecules of interest can be conjugated with oligomeric DNA independently.

Dendron surface modification of the tips and substrates allows the AFM to pick a single DNA reproducibly. The successful conjugation of a new DNA at the apex of the tip through the specific hybridization and the subsequent ligation provide a novel approach for introducing a single copy of various molecules at the tip.

Linker

As stated herein, the present inventors have discovered that using a dendron as a linker allows a sufficient spacing to attach five or less, typically three or less, and often a single oligonucleotide on an AFM tip. Suitable dendrons comprise a plurality of functional groups (i.e., substrate bound functional groups) that are used to attach the dendron to a solid substrate surface and a linker functional group (i.e., oligonucleotide bound functional group) that is used to attach an oligonucleotide moiety. Generally, useful dendrons comprise at least nine, typically at least eighteen, often twenty seven substrate bound functional groups. Suitable substrate bound functional groups include, but are not limited to, carboxylates, amines, hydroxyl groups, thiol groups, carbamides, and other suitable functional groups well known to one skilled in the art.

In many instances, the linker is of the formula:

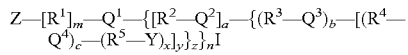

wherein
each of m, a, b, and c is independently 0 or 1;
x is 1 when c is 0 or when c is 1, x is an integer from 1 to the oxidation state of $Q^4-1$;
y is 1 when b is 0 or when b is 1, y is an integer from 1 to the oxidation state of $Q^3-1$;
z is 1 when a is 0 or when a is 1, z is an integer from 1 to the oxidation state of $Q^2-1$;
n is an integer from 1 to the oxidation state of $Q^1-1$;
$Q^1$ is a central atom having the oxidation state of at least 3;
each of $Q^2$, $Q^3$ and $Q^4$ is independently a branch atom having the oxidation state of at least 3;
each of $R^1$, $R^2$, $R^3$, $R^4$, and $R^5$ is independently a linker;
Z is the functional group that is attached to an oligonucleotide; and
each of Y is independently a substrate bound functional group,
provided the product of n, x, y, and z is at least 3.

It should be appreciated that when a, b or c is 1 and the corresponding z, y or x is less than the oxidation state of $Q^2-1$, $Q^3-1$ or $Q^4-1$, respectively, the remaining atoms attached to $Q^2$, $Q^3$, or $Q^4$, respectively, is hydrogen. As used herein, "Q" refers to any one of or all of $Q^1$, $Q^2$, $Q^3$, $Q^4$. Typically, Q is any atom in group IVA or VA of the periodic table. Exemplary atoms for Q include, but are not limited to, N, P, C, Si, Ge, and the like. Often, Q is N, P, C, or Si.

As can be seen in Formula I, Z is attached to the central atom optionally through a linker $R^1$. Often a is 1 such that Z is attached to the central atom through a linker $R^1$.

Yet in other embodiments, Z comprises a heteroatom selected from the group consisting of N, O, S, P, and a combination thereof.

Each Y can be independently a substrate bound function group. That is, each Y can be independent of the other Y group. Often, however, all of the Y's are the same functional group. However, in general Z and Y are different functional groups. In some instances, Z and Y can be the same functional group, but one or the other is in a protected form. Such differences in functional group and/or the presence of a protecting group allow one to distinguish the reactivity of Z and Y, thereby allowing one to attach the dendron to the solid support via a plurality of Y's and allows attachment of an oligonucleotide on Z.

Each of linkers $R^1$, $R^2$, $R^3$, $R^4$, and $R^5$ can be the same or different. As used herein, when "R" is used to denote a linker generically, it can refer to $R^1$, $R^2$, $R^3$, $R^4$, $R^5$, or any combination thereof. Typically, each linker is a repeating unit, a linear or branched organic moiety. However, it is also understood that not all the linkers need to be the same repeating unit. Nor do all valence positions for a linker need be filled with a repeating unit. For example, all of the $R^2$ can be the same repeating units. Or one or two of the $R^2$ may be a repeating unit, and the remaining $R^2$'s may be H or other chemical entities Likewise, one or two of each of $R^3$, $R^4$, or $R^5$ may be, independently, a repeating unit, H or any other chemical entity. Thus, a variety of polymers are within the scope of the invention. Accordingly, it is possible that a dendron can have from about 3 to about 81 Y functional groups. Generally, the dendron has from about 6 to about 81 Y functional groups, typically from about 6 to about 54 Y functional groups, often from about 6 to about 27 Y functional groups, and more often from about 9 to about 27 Y functional groups.

Table 1 below lists various types of exemplified dendrons. However, it is to be understood that variations in $Z^a$, $R^1$, Q, R and $Y^a$ are encompassed by the present invention. It should be noted that in Table 1, the term $Z^a$ refers to a protected form of oligonucleotide bound functional group and $Y^a$ refers to a substrate bound functional group prior to being bound to the solid substrate surface. Accordingly, in some instances $Z^a$ and/or $Y^a$ need to be deprotected prior to being bound to an oligonucleotide and the solid substrate surface, respectively.

TABLE 1

Representative and Exemplified Macromolecule Compounds

| $Z^a$ | $R^1$ | Q | R | $Y^a$ |
|---|---|---|---|---|
| A-NH— | —$(CH_2)_3C(O)NH$ | C | $CH_2O(CH_2)_2C(O)$ | OH |
| A-NH— | —$(CH_2)_3C(O)NH$ | C | $CH_2O(CH_2)_2C(O)$ | OMe |
| Boc-NH— | —$(CH_2)_3C(O)NH$ | C | $CH_2O(CH_2)_2C(O)$ | OH |
| Boc-NH— | —$(CH_2)_3C(O)NH$ | C | $CH_2O(CH_2)_2C(O)$ | OMe |
| A-NH— | —$(CH_2CH_2O)_2CH_2C(O)NH$ | C | $CH_2O(CH_2)_2C(O)$ | OH |
| A-NH— | —$(CH_2CH_2O)_2CH_2C(O)NH$ | C | $CH_2O(CH_2)_2C(O)$ | OMe |
| A-NH— | —$(CH_2)_3C(O)NH$ | C | $CH_2O(CH_2)_2C(O)$ | OH |
| Boc-NH— | -(cyclohexyl)(CO)$CH_2$ | C | $(CH_2)_2$-(cyclohexyl)-C(O) | $NH_2$ |
| Boc-NH— | —$(CH_2CH_2O)_2CH_2C(O)NH$ | C | $CH_2O(CH_2)_2C(O)$ | OH |

TABLE 1-continued

Representative and Exemplified Macromolecule Compounds

| $Z^a$ | $R^1$ | Q | R | $Y^a$ |
|---|---|---|---|---|
| Fmoc-NH— | —(CH$_2$)$_6$NHC(O)NH | C | CH$_2$—C≡C—CH$_2$C(O) | OH |
| Fmoc-NH— | —(CH$_2$)$_7$C(O)O | C | CH$_2$—C≡C—CH$_2$C(O) | OMe |
| Ns-NH— | -(cyclohexyl)(CO)O | C | CH$_2$O(CH$_2$)$_2$C(O) | NH$_2$ |
| Ns-NH— | —(CH$_2$)$_6$NHC(O)NH | C | (CH2)$_7$ | NH$_2$ |
| A-NH— | —(CH$_2$)$_3$C(O)NH | C | CH$_2$O(CH$_2$)$_2$C(O) | OH |
| Boc-NH— | —(CH$_2$)$_7$C(O)NH | C | (CH2)$_2$C(O) | OH |
| Ns-NH— | —(CH$_2$)$_6$(CO)NH | C | (CH2)$_2$-(cyclohexyl)-C(O) | OH |
| Fmoc-NH— | —(CH$_2$)$_6$(CO)O | C | CH$_2$—C≡C—CH$_2$C(O) | NH$_2$ |
| Fmoc-NH— | —(CH$_2$)$_6$NH(CO)O | C | (CH2)$_2$-(cyclohexyl)-C(O) | OH |
| Ns-NH— | -(cyclohexyl)(CO)O | C | CH$_2$OCH(CH$_3$)CH$_2$C(O) | NH$_2$ |
| Boc-NH— | -(cyclopropyl)(CO)O | C | CH$_2$—C≡C—CH$_2$C(O) | NH$_2$ |
| A-NH— | —(CH$_2$)$_3$C(O)NH | C | CH$_2$O(CH$_2$)$_2$C(O) | OH |
| A-NH— | —(CH$_2$)$_3$C(O)NH | C | CH$_2$O(CH$_2$)$_2$C(O) | OMe |
| A-NH— | —(CH$_2$CH$_2$O)$_2$CH$_2$C(O)NH | C | CH$_2$O(CH$_2$)$_2$C(O) | OH |
| A-NH— | —(CH$_2$CH$_2$O)$_2$CH$_2$C(O)NH | C | CH$_2$O(CH$_2$)$_2$C(O) | OMe |
| Fmoc-NH— | —(CH$_2$)$_6$C(O)NH | C | CH$_2$O(CH$_2$)$_2$C(O) | OH |
| Fmoc-NH— | —(CH$_2$)$_6$C(O)NH | C | CH$_2$O(CH$_2$)$_2$C(O) | OMe |
| Boc-NH— | —(CH$_2$)$_3$C(O)NH | C | CH$_2$O(CH$_2$)$_2$C(O) | OH |
| Boc-NH— | —(CH$_2$)$_3$C(O)NH | C | CH$_2$O(CH$_2$)$_2$C(O) | OMe |
| Ns-NH— | —(CH$_2$)$_3$C(O)NH | C | CH$_2$O(CH$_2$)$_2$C(O) | OH |
| Ns-NH— | —(CH$_2$)$_3$C(O)NH | C | CH$_2$O(CH$_2$)$_2$C(O) | OMe |
| A-NH— | —(CH$_2$)$_6$NHC(O)CH$_2$CH$_2$ | C | (CH2)$_7$ | OBzl |
| A-NH— | —(CH$_2$)$_3$C(O)NH | C | CH$_2$O(CH$_2$)$_2$C(O) | OH |
| Fmoc-NH— | —(CH$_2$)$_6$NHC(O)NH | C | (CH2)$_2$-(cyclohexyl)-C(O) | NH$_2$ |
| Boc-NH— | -(cyclohexyl)(CO)O | C | CH$_2$—C≡C—CH$_2$C(O) | OMe |
| Boc-NH— | —(CH$_2$)$_5$NH | C | CH$_2$OCH(CH$_3$)CH$_2$C(O) | NH$_2$ |
| Ns-NH— | -(cyclopropyl)(CO)CH$_2$ | C | (CH2)$_2$ | NH$_2$ |
| Ns-NH— | —(CH$_2$)$_6$C(O)O | C | CH$_2$OCH$_2$CH(CH$_3$)C(O) | NH$_2$ |
| Fmoc-NH— | —(CH$_2$)$_6$NHC(O)O | C | CH$_2$OCH(CH$_3$)CH$_2$C(O) | NH$_2$ |
| Boc-NH— | —(CH$_2$)$_3$C(O)NH | C | CH$_2$O(CH$_2$)$_2$C(O) | NH$_2$ |
| Boc-NH— | -(cyclohexyl)(CO)CH$_2$ | C | (CH2)$_2$-(cyclohexyl)-C(O) | OH |
| Fmoc-NH— | —(CH$_2$CH$_2$O)$_2$CH$_2$C(O)O | C | CH$_2$O(CH$_2$)$_2$C(O) | OH |
| Fmoc-NH— | —(CH$_2$)$_6$NHC(O)NH | C | (CH$_2$)$_2$-(cyclohexyl)-C(O) | NH$_2$ |
| Ns-NH— | -(cyclohexyl)(CO)NH | C | CH$_2$—C≡C—CH$_2$C(O) | OH |
| Ns-NH— | -(cyclopropyl)(CO)CH$_2$ | C | CH$_2$O(CH$_2$)$_2$C(O) | OMe |
| A-NH— | -(cyclopropyl)(CO)CH$_2$ | C | CH$_2$OCH(CH$_3$)CH$_2$C(O) | OH |
| A-NH— | -(cyclopropyl)(CO)CH$_2$ | C | CH$_2$OCH$_2$CH(CH$_3$)C(O) | NH$_2$ |
| A-NH— | —(CH$_2$)$_5$O | C | CH$_2$OCH$_2$CH(CH$_3$)C(O) | OH |
| A-NH— | —(CH$_2$)$_3$C(O)NH | C | CH$_2$O(CH$_2$)$_2$C(O) | OH |
| Fmoc-NH— | -(cyclohexyl)(CO)O | C | CH$_2$OCH(CH$_3$)CH$_2$C(O) | NH$_2$ |
| Boc-NH— | -(cyclopropyl)(CO)O | C | CH$_2$OCH$_2$CH(CH$_3$)C(O) | NH$_2$ |
| Fmoc-NH— | —(CH$_2$)$_6$NHC(O)CH$_2$NH | C | (CH2)$_2$-(cyclohexyl)-C(O) | OH |
| Ns-NH— | —(CH$_2$)$_6$NHC(O)CH$_2$ | C | CH$_2$—C≡C—CH$_2$C(O) | OMe |
| Boc-NH— | —(CH$_2$)$_5$O | C | CH$_2$OCH$_2$CH(CH$_3$)C(O) | NH$_2$ |
| A-NH— | —(CH$_2$)$_3$C(O)NH | C | CH$_2$O(CH$_2$)$_2$C(O) | OH |
| A-NH— | —(CH$_2$)$_6$NHC(O)CH$_2$CH$_2$ | C | (CH2)$_7$ | OH |
| Fmoc-NH— | —(CH$_2$CH$_2$O)$_2$CH$_2$C(O)O | C | (CH2)$_2$-(cyclohexyl)-C(O) | NH$_2$ |
| Ns-NH— | -(cyclopropyl)(CO)NH | C | (CH2)$_2$-(cyclohexyl)-C(O) | NH$_2$ |
| Boc-NH— | -(cyclohexyl)(CO)CH$_2$ | C | CH$_2$OCH(CH$_3$)CH$_2$C(O) | OMe |
| Fmoc-NH— | —(CH$_2$)$_5$O | C | CH$_2$OCH$_2$CH(CH$_3$)C(O) | NH$_2$ | where A = anthracenemethyl, Fmoc = 9-fluorenylmethyloxycarbonyl, Boc = tert-butoxycarbonyl, and Ns = 2-nitrophenylsulfonyl.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

General Methods

The silane coupling agent N-(3-(triethoxysilyl)propyl)-O-polyethyleneoxide urethane was purchased from Gelest (Morrisville, Pa., USA). All other chemicals, including a 5-nm AuNP colloid solution, are of reagent grade purchased from Sigma-Aldrich (St Louis, Mo.). UV-grade fused silica plates were purchased from CVI Laser. Polished Si (100) wafers (dopant: phosphorus; resistivity: 1.5-2.1·cm) were purchased from MEMC Electronic Materials (St. Peters, Mo., USA). Deionized water (18 M·cm) was obtained by passing distilled water through a Barnstead E-pure 3-Module system. All oligonucleotides were purchased from Bionics (Korea). The AFM probes for TEM imaging were purchased from Applied NanoStructures (SICON, k=0.2 N/m) (Santa Clara, Calif., USA) and μmasch (Portland, Oreg., USA) (CSC38, CSC17/Si3N4/noA1, k=0.1~0.3 N/m). Tips from Applied Nanostructures were used for optimizing the picking condition and investigating the influence of the tip velocity. Tips from μmasch were used for investigating the influence of the tip radius. For the force measurement, silicon nitride AFM probes were purchased from NanoInk, Inc. (Skokie, Ill., USA) (PEN-0012-03, k=0.004 N/m). The aldehyde-terminated slides were purchased from Arrayit Corporation (SuperAldehyde). (Sunnyvale, Calif., USA) T4 DNA ligase was purchased from Takara Inc (Otsu, Shiga, Japan). Transmittance Electron Microscopy (JEM-1011, JEOL, Japan) was used to image the silicon tips.

Preparation of the Tips and Substrates

AFM probes and silicon wafers were treated as described previously (see FIGS. 5A-B). See, for example, Jung et al., *J. Am. Chem. Soc.* 2007, 129, 9349-9355; and Jung et al., *Nucleic Acids Res.* 2009, 37, e10.

Gold-Labeled DNA

The previously reported preparation method was adopted to prepare the DNA-AuNP conjugates. See, for example, Zanchet et al., *Nano Lett.* 2001, 1, 32-35. Briefly, bis(para-sulfonatophenyl)phenylphosphine dehydrate dipotassium salt (1.0 mg) was added to the gold nanoparticle (AuNP) solution (10 mL), and the solution was incubated at 22° C. overnight. The AuNPs were then precipitated by adding solid NaCl until the solution color turned blue. After centrifugation, the supernatant was removed, and the AuNPs were redispersed in 0.5×TBE buffer. The resulting concentration of the AuNPs was 2 μM. The AuNP solution was then mixed with a DNA solution at a molar ratio of 1:1 and incubated at 22° C. overnight. Subsequently, the sample was injected into 3% agarose gel, and electrophoresis was performed with 0.5× TBE running buffer (see FIG. 7). The band corresponding to the AuNPs conjugated with a single DNA was cut from the gel, and the gel pad was placed in a dialysis tube filled with 0.5×TBE buffer. After applying a voltage (100 V/15 cm) for 20 min, the solution was transferred to a centrifugation tube, and the volume was adjusted to 11.5 mL with the running buffer. After centrifugation, the supernatant was discarded, and DNA-AuNP conjugates were redispersed in a 0.5×TBE buffer containing 50 mM NaCl. UV-vis spectroscopy showed that the concentration of the resulting solution was $1\times10^2$ nM.

Hybridization of DNA-AuNP Conjugates with Probe DNAs

Substrates immobilizing the probe DNA were incubated overnight in the above conjugate solution at room temperature. The substrates were then washed with 20 ml of a 0.5× TBE buffer solution (pH 8.0) containing 50 mM NaCl and shaken gently in a 0.5×TBE buffer solution at 37° C. After washing, the substrates were stored in a 0.5×TBE buffer solution (pH 8.0) containing 50 mM NaCl until the picking experiment.

Materials for Control Experiments

Silicon wafers and AFM probes were treated with (3-aminopropyl)diethoxy-methylsilane (APDES) as described previously by Jung et al. in *J. Am. Chem. Soc.* 2007, 129, 9349-9355. Subsequent treatment with a linker, N,N'-disuccinimidyl carbonate, and conjugation with DNAs were performed as described elsewhere. See, for example, Jung et al., *J. Am. Chem. Soc.* 2007, 129, 9349-9355.

Picking AuNP-DNA Conjugates

All picking experiments were performed with a NanoWizard AFM (JPK Instrument) (Berlin, Germany), and carried out in a fresh 0.5×TBE buffer solution (pH 8.0) containing NaCl (50 mM) at room temperature. The tip velocity was fixed at 0.2 μm/s, the z-range was set to 500 nm, and it took 5 s to complete a cycle. The picking was carried out in autoscan mode, and for every case the picking process took <5 min. To investigate an influence of tip velocity, velocities of 0.01 μm/s and 10 μm/s were also examined.

Second Hybridization with the AFM Tips

The sequence of another thiolated DNA was selected to hybridize with the ss DNA part (20-bp) of the picked AuNP-DNA conjugate. For proper isolation, an oligocytosine (30-bp) was added to the 5' position of the new thiolated DNA (see FIG. 7). The new AuNP-DNA conjugate was prepared and isolated using the same method as described above. After picking the first AuNP-DNA conjugate, the tip was immediately transferred to a solution containing the second AuNP-DNA conjugates, and incubated for 1 h at room temperature. Subsequently, the tip was washed with 20 ml of a 0.5×TBE buffer solution (pH 8.0) containing 50 mM of NaCl, then shaken gently in a 0.5×TBE buffer solution at 37° C. Tip images were taken with TEM.

Ligation

The tips picked up the target DNA from the substrate were placed in a solution containing the 20 mer DNA (40 μM, Tris-HCl buffer from Takara Inc. (pH7.6)) for 1 hr at room temperature. Subsequently, T4 DNA ligase (10 units) was added into the solution, and 12 h at room temperature were allowed. After the ligation, the tips were placed in deionized water heated at 90° C. for 1 h. The tips were rinsed with deionized water at room temperature and dried under vacuum.

AFM Force Measurement

All force measurements were performed with the NanoWizard AFM (JPK instrument). The spring constant of each tip was calibrated using the thermal fluctuation method right before each experiment. The spring constants of the cantilevers employed varied between 0.006 and 0.008 N/m. All measurements were carried out in PBS buffer and the loading rate was 0.54 μm sec$^{-1}$. More than 100 force-distance curves were recorded per spot and more than 5 spots were examined for each tip.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

SEQUENCE LISTING

```
<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: Figure 1B Picker DNA 5' to 3'
```

<400> SEQUENCE: 1
gcctgctggt gtggaaccgt gactgtcgat gccgcgctcg                          40

<210> SEQ ID NO 2
<211> LENGTH: 35
<212> TYPE: DNA
<213> ORGANISM: Artificial Sequence
<220> FEATURE:
<223> OTHER INFORMATION: Figure 1B Probe DNA 5' to 3'

<400> SEQUENCE: 2
tatgtggtat tatttcttga cccccccccc ccccc                               35

<210> SEQ ID NO 3
<211> LENGTH: 63
<212> TYPE: DNA
<213> ORGANISM: Artificial Sequence
<220> FEATURE:
<223> OTHER INFORMATION: FIgure 1B Target DNA 3' to 5'

<400> SEQUENCE: 3
cggacgacca caccttggca ctgacagcta cggcgcgagc atacaccata ataaagaact    60
ccc                                                                 63

<210> SEQ ID NO 4
<211> LENGTH: 40
<212> TYPE: DNA
<213> ORGANISM: Artificial Sequence
<220> FEATURE:
<223> OTHER INFORMATION: Figure 3 Picker DNA 5' to 3'

<400> SEQUENCE: 4
gcctgctggt gtggaaccgt gactgtcgat gccgcgctcg                          40

<210> SEQ ID NO 5
<211> LENGTH: 50
<212> TYPE: DNA
<213> ORGANISM: Artificial Sequence
<220> FEATURE:
<223> OTHER INFORMATION: Figure 3 Probe DNA 3' to 5'

<400> SEQUENCE: 5
agttctttat tatggtgtat cccccccccc cccccccccc cccccccccc               50

<210> SEQ ID NO 6
<211> LENGTH: 63
<212> TYPE: DNA
<213> ORGANISM: Artificial Sequence
<220> FEATURE:
<223> OTHER INFORMATION: Figure 3 Target DNA 3' to 5'

<400> SEQUENCE: 6
cggacgacca caccttggca ctgacagcta cggcgcgagc atacaccata ataaagaact    60
ccc                                                                 63

Figure 6C:
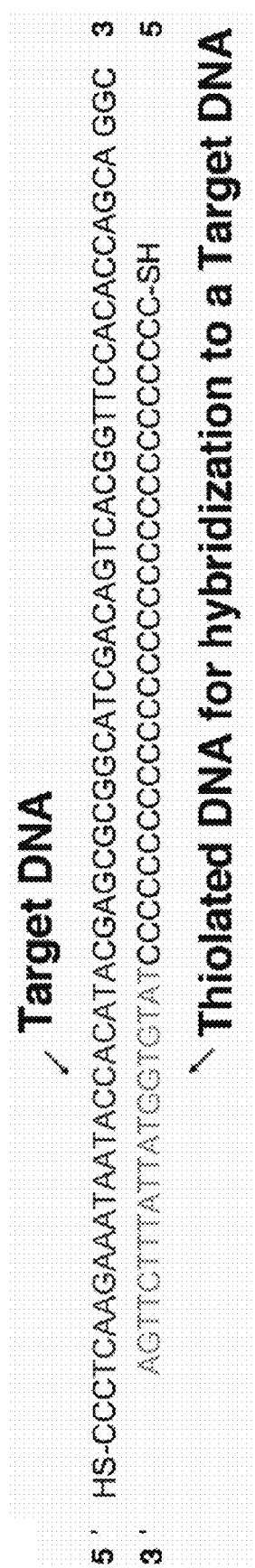
FIG. 6C shows the matching part of the target DNA (SEQ ID NO:7) and the probe DNA (SEQ ID NO:8) that are used for the second hybridization.

<210> SEQ ID NO 7
<211> LENGTH: 63
<212> TYPE: DNA
<213> ORGANISM: Artificial Sequence
<220> FEATURE:
<223> OTHER INFORMATION: Figure 6C Target DNA 5' to 3'

<400> SEQUENCE: 7

```
ccctcaagaa ataataccac atacgagcgc ggcatcgaca gtcacggttc cacaccagca    60
ggc                                                                  63
```

<210> SEQ ID NO 8
<211> LENGTH: 50
<212> TYPE: DNA
<213> ORGANISM: Artificial Sequence
<220> FEATURE:
<223> OTHER INFORMATION: Figure 6C Thiolated Hybridization DNA 3' to 5'

<400> SEQUENCE: 8

```
agttctttat tatggtgtat ccccccccc ccccccccc ccccccccc                  50
```

What is claimed is:

1. A method for producing a single surface bound probe oligonucleotide on a first solid substrate that comprises a plurality of first oligonucleotides, said method comprising:
   contacting only one of the plurality of first oligonucleotides bound to said first solid substrate with a target oligonucleotide that is hybridized to a second oligonucleotide on a second solid substrate under conditions sufficient to produce a single first oligonucleotide-second oligonucleotide-target oligonucleotide complex, wherein the target oligonucleotide comprises an oligonucleotide sequence that is complementary to the first and second oligonucleotide sequences, and wherein said second solid substrate comprises a plurality of second oligonucleotide-target oligonucleotide complexes;
   removing said second oligonucleotide from said single first oligonucleotide-second oligonucleotide-target oligonucleotide complex under conditions sufficient to produce a single first oligonucleotide-target oligonucleotide complex on said first solid substrate
   contacting said first oligonucleotide-target oligonucleotide complex with a third oligonucleotide under conditions sufficient to produce a segmented hybridized oligonucleotide complex, wherein said segmented hybridized oligonucleotide complex comprises a first oligonucleotide-third oligonucleotide-target oligonucleotide complex, wherein said third oligonucleotide comprises an oligonucleotide sequence that is complementary to an unhybridized portion of said target oligonucleotide;
   contacting said segmented hybridized oligonucleotide complex with a ligase under conditions sufficient to covalently link said first oligonucleotide and said third oligonucleotide to produce a first solid substrate bound oligonucleotide complex comprising a surface bound probe oligonucleotide-target oligonucleotide complex; and
   removing said target oligonucleotide from said probe oligonucleotide-target oligonucleotide complex to produce said first solid substrate comprising a single surface bound probe oligonucleotide, wherein said probe oligonucleotide comprises a nucleotide sequence that is complementary to the nucleotide sequence of the target oligonucleotide.

2. The method of claim 1, wherein said third oligonucleotide further comprises an additional oligonucleotide such that said segmented hybridized oligonucleotide complex comprises at least a portion of said third oligonucleotide that is not hybridized to the target oligonucleotide.

3. The method of claim 1, wherein the amount of hybridized nucleotide sequences in said first oligonucleotide is higher than the amount of hybridized nucleotide sequences in said second oligonucleotide.

4. The method of claim 1, wherein the first oligonucleotide is bound to the first solid substrate by a first linker.

5. The method of claim 4, wherein the first linker comprises a dendron.

6. The method of claim 5, wherein the dendron is of the formula:

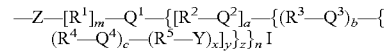

wherein
   each of m, a, b, and c is independently 0 or 1;
   x is 1 when c is 0 or when c is 1, x is an integer from 1 to the oxidation state of $Q^4$-1;
   y is 1 when b is 0 or when b is 1, y is an integer from 1 to the oxidation state of $Q^3$-1;
   z is 1 when a is 0 or when a is 1, z is an integer from 1 to the oxidation state of $Q^2$-1;
   n is an integer from 1 to the oxidation state of $Q^{1-1}$;
   $Q^1$ is a central atom having the oxidation state of at least 3;
   each of $Q^2$, $Q^3$ and $Q^4$ is independently a branch atom having the oxidation state of at least 3;
   each of $R^1$, $R^2$, $R^3$, $R^4$, and $R^5$ is independently a linker;
   Z is a functional group linked to the first oligonucleotide; and
   each of Y is independently a functional group, wherein a plurality of Y are attached to the
   first solid substrate surface, provided the product of n, x, y, and z is at least 3.

7. The method of claim 6, wherein Z comprises a heteroatom selected from the group consisting of N, O, S, P, and a combination thereof 8. The method of claim 6, wherein Z comprises a functional group selected from the group consisting of —NR—C(=X)—O—, —O—C(=X)—O—, —NR —C(=X)—, —O—C(=X)—, wherein X is N, O, or S, and R is hydrogen, alkyl, cycloalkyl, aralkyl, aryl, or (cycloalkyl)alkyl.

9. The method of claim 6, wherein each of $R^1$, $R^2$, $R^3$, $R^4$, and $R^5$ is independently a linker comprising 4 to 20 linker chain atoms, wherein each linker chain atom is independently selected from the group consisting of C, O, N, S, and P.

10. The method of claim 1, wherein said first solid substrate is an atomic force microscope tip.

11. The method of claim 1, wherein said probe oligonucleotide further comprises a tethered moiety.

12. The method of claim 11, wherein the tethered moiety comprises a label, a ligand, a peptide, or a combination thereof.

13. A method for attaching one single-stranded oligonucleotide probe on an atomic force microscope (AFM) tip surface, said method comprising:

contacting an AFM tip comprising a plurality of single-stranded first oligonucleotides attached to its surface with a partially hybridized oligonucleotide complex under conditions sufficient to produce one first hybridized complex on said AFM tip surface, wherein said partially hybridized oligonucleotide complex comprises a single-stranded second oligonucleotide that is hybridized to a portion of a single-stranded target oligonucleotide, and wherein said first hybridized complex comprises said first oligonucleotide that is attached to said AFM tip and said second oligonucleotide both of which are hybridized to said target oligonucleotide;

removing said second oligonucleotide from said first hybridized complex under conditions sufficient to produce a first partially hybridized complex;

contacting said first partially hybridized complex with a third oligonucleotide under conditions sufficient to produce one segmented hybridized double-stranded oligonucleotide complex, wherein said segmented hybridized double-stranded oligonucleotide complex comprises said first oligonucleotide and said third oligonucleotide that are hybridized to said target oligonucleotide;

contacting said segmented hybridized double-stranded oligonucleotide complex with a ligase under conditions sufficient to covalently link said first oligonucleotide and said third oligonucleotide to produce an AFM tip comprising a single surface bound double-stranded oligonucleotide complex; and subjecting said AFM tip surface bound double-stranded oligonucleotide complex to conditions sufficient to remove said target oligonucleotide from said double-stranded oligonucleotide complex to produce said AFM tip having one single-stranded oligonucleotide probe, wherein said oligonucleotide probe comprises nucleotide sequences of said first oligonucleotide and said third oligonucleotide.

* * * * *